(12) United States Patent
Tanase et al.

(10) Patent No.: US 7,737,069 B2
(45) Date of Patent: Jun. 15, 2010

(54) MAGNESIUM COMPOUND, CATALYST FOR OLEFIN POLYMERIZATION AND METHOD FOR PRODUCING OLEFIN POLYMER

(75) Inventors: Shojiro Tanase, Ichihara (JP); Nobuhiro Yabunouchi, Sodegaura (JP); Takehito Konakazawa, Ichihara (JP); Takanori Sadashima, Sumida-ku (JP); Kiyokazu Katayama, Ichihara (JP); Kenji Tanaka, Ichihara (JP); Hideaki Noda, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 704 days.

(21) Appl. No.: 11/547,281

(22) PCT Filed: Apr. 19, 2005

(86) PCT No.: PCT/JP2005/007478

§ 371 (c)(1),
(2), (4) Date: Oct. 4, 2006

(87) PCT Pub. No.: WO2005/102973

PCT Pub. Date: Nov. 3, 2005

(65) Prior Publication Data

US 2008/0281059 A1 Nov. 13, 2008

(30) Foreign Application Priority Data

| Apr. 23, 2004 | (JP) | 2004-128153 |
| Aug. 24, 2004 | (JP) | 2004-243595 |
| Aug. 31, 2004 | (JP) | 2004-252958 |
| Sep. 14, 2004 | (JP) | 2004-266256 |

(51) Int. Cl.
B01J 31/00 (2006.01)

(52) U.S. Cl. .............. 502/102; 502/103; 502/111; 502/115; 502/116; 502/9

(58) Field of Classification Search ............. 526/124.2, 526/124.3; 502/116, 9, 102
See application file for complete search history.

(56) References Cited

U.S. PATENT DOCUMENTS

| 4,663,299 A * | 5/1987 | Chadwick et al. ............ 502/9 |
| 5,227,542 A * | 7/1993 | Horns et al. ............ 568/851 |
| 5,556,820 A | 9/1996 | Funabashi et al. |
| 5,594,079 A * | 1/1997 | Hara et al. ............ 526/119 |
| 6,065,715 A | 5/2000 | Andersson |
| 6,596,824 B2 * | 7/2003 | Nambu et al. ............ 526/82 |

FOREIGN PATENT DOCUMENTS

| EP | 0 216 402 A2 | 4/1987 |
| EP | 0 268 274 A2 | 5/1988 |
| EP | 0 398 698 A2 | 11/1990 |
| EP | 1 061 088 A1 | 12/2000 |
| EP | 1 090 957 A1 | 4/2001 |
| EP | 1 298 149 A1 | 4/2003 |
| EP | 1 508 559 A1 | 2/2005 |
| EP | 1 775 309 A1 | 4/2007 |
| JP | 58-811 | 1/1983 |
| JP | 63-280707 | 11/1988 |
| JP | 03-074341 | 3/1991 |
| JP | 4-130107 | 5/1992 |
| JP | 04-370104 | 12/1992 |
| JP | 09-025316 | 1/1997 |
| JP | 09-059321 | 3/1997 |
| JP | 09-067416 | 3/1997 |
| JP | 09-506319 | 6/1997 |
| JP | 10-287710 | 10/1998 |
| JP | 11 246620 | 9/1999 |
| JP | 2002-030128 | 1/2002 |
| WO | 03-099749 | 12/2003 |
| WO | 2004 018529 | 3/2004 |

OTHER PUBLICATIONS

U.S. Appl. No. 11/816,587, filed Aug. 17, 2007, Tanase, et al.
U.S. Appl. No. 12/408,926, filed Mar. 23, 2009, Tanase, et al.

* cited by examiner

*Primary Examiner*—Patrick Ryan
*Assistant Examiner*—Ladan Mohaddes
(74) *Attorney, Agent, or Firm*—Oblon, Spivak, McClelland, Maier & Neustadt, L.L.P.

(57) ABSTRACT

A magnesium compound represented by the formula (I):

$$Mg(OC_2H_5)_{2-n}(OR^1)_n \quad (I)$$

where $R^1$ is $C_mH_{2m+1}$ (where m is an integer of from 3 to 10), and n is a numerical value satisfying $0<n<0.35$; a solid catalyst component for olefin polymer using the magnesium compound; a catalyst for olefin polymer; and methods of producing olefin copolymers such as a propylene-based random copolymer and propylene-based block copolymer by using the catalyst for olefin polymer.

5 Claims, 5 Drawing Sheets

MAGNESIUM COMPOUND, CATALYST FOR OLEFIN POLYMERIZATION AND METHOD FOR PRODUCING OLEFIN POLYMER

CROSS REFERENCE TO RELATED APPLICATION

This application is a 371 of PCT/JP05/007478, filed on Apr. 19, 2005, and claims priority to the following Japanese Patent Applications: JP 2004-128153, filed on Apr. 23, 2004; JP 2004-243595, filed on Aug. 24, 2004; JP 2004-252958, filed on Aug. 31, 2004; and JP 2004-266256, filed on Sep. 14, 2004.

TECHNICAL FIELD

The present invention relates to a magnesium compound and a method of producing the same, a solid catalyst component for olefin polymerization, and a catalyst for olefin polymerization. And, the present invention relates to a method of producing an olefin polymer including homopolymer and copolymer.

The present invention relates to a propylene-based random copolymer and a method of producing the same. In particular, the present invention relates to a film which has low stickiness, and excels in low-temperature heat sealing property and impact resistance, and a method of producing the same.

The present invention relates to propylene-based block copolymer particles excellent in the flow property of the particles and a method of producing the same. In particular, the present invention relates to propylene-based block copolymer particles useful for the fields such as automobile parts, home electric appliance and use for foods, in which stiffness and low temperature impact resistance are required, excellent in flow property, and not so hard to produce the same.

TECHNICAL BACKGROUND

Hitherto, magnesium chloride and magnesium alkoxides have been widely used as a support material without being milled in the field of catalysts for olefin polymerization, specifically the homopolymerization or copolymerization of ethylene, propylene or the like. This may improve the catalyst activity and the morphology of polymer powder.

For example, for improving an obtained polymer in the morphology including a particle size, form, etc., a method in which a magnesium compound is supported on an inorganic oxide such as silica (for instance, see JP-A-S63-280707), or a method in which a magnesium compound is once dissolved in a solvent such as an alcohol and then precipitate again, which precipitate is used (for instance, see JP-A-S58-000811) is known.

However, these methods include very complicated steps, since they require the procedures of supporting, dissolving and precipitating a magnesium compound. Further, these methods have a defect that the catalyst is poor in stability of performance.

To use as a support of catalysts a magnesium compound obtained by reacting metal magnesium, an alcohol such as ethanol and a certain amount of halogen (for instance, see JP-A-H4-130107) is disclosed. However, the form (surface smoothness) of the polymer powder may not be satisfactory dependently on the polymerization conditions of this method.

A method in which metal magnesium and ethanol are reacted without solvent in the presence of iodine, followed by maintaining the reaction product for a few hours under reflux of an alcohol to prepare a catalyst is disclosed (for instance, see JP-A-H3-074341). However, by this method, the smoothness of the support to be obtained is not satisfactory.

A magnesium compound which is obtained by reacting metal magnesium and ethanol in the presence of iodine and which satisfies the sphericity S<1.60 and the particle size distribution index P<5.0 is disclosed (for instance, see JP-A-H4-370104). However, although the support is excellent in the sphericity and particle size distribution, when catalyst components are supported on the support and polymerization is carried out, resultant powder particles sometimes fracture.

A magnesium compound having the sphericity S<4.0, which is obtained by reacting metal magnesium, ethanol and iodine, is disclosed (for instance, see WO03/099749). However, although the magnesium compound has narrow particle size distribution and small sphericity, usable raw material magnesium is strictly limited.

A propylene-based random copolymer obtained by copolymerizing propylene and the other α-olefins has impact resistance and transparency superior to a propylene homopolymer, further has relatively low melting point so that it is excellent in low temperature heat sealing property. Therefore, the propylene-based random copolymer has been widely used for uses mainly including the field of packaging material such as various types of films.

As propylene-based random copolymers, for example, a random copolymer of propylene and ethylene, a random copolymer of propylene and an α-olefin having at least 4 carbon atoms, and a ternary random copolymer of propylene, ethylene and an α-olefin having at least 4 carbon atoms are known.

As to the above-mentioned propylene-based random copolymer, the larger the ratio of monomer copolymerized with propylene is, the more the melting point can be lowered, and it has been known that the impact resistance and low temperature heat sealing property are improved. On the other hand, as the composition ratio of the copolymerizable monomer increases, the amount of low molecular weight amorphous components having tacky nature increases, the amount of tackiness components at the time of forming a film increases and the blocking resistance tends to deteriorate. As the result, there are inadequacies that the commercial value is sometimes reduced and its use is limited dependently on the use.

Further, for producing a propylene-based random copolymer, a catalyst for olefin polymerization consisting of a solid titanium catalyst component, an organic aluminum compound and, if necessary an electron donating compound has been widely used (for instance, JP-A-H9-025316, JP-A-H9-059321, JP-A-H9-067416 and JP-A-H10-287710). However, in the case of producing it using a hydrocarbon solvent or propylene as a medium, there sometimes has problems that copolymer particles adhere to each other because of increase of the amount of the by-product low molecular weight amorphous components, that the productivity decreases because of increase of the viscosity of the polymerization system, and that in some cases, serious troubles occur in the production.

When the production is carried out by gas phase polymerization, in addition to increase of low molecular weight amorphous components and decrease of the melting point, the particles tend to melt by the enlarged heat of reaction involved with increase of the reaction rate, the copolymerization particles adhere to each other or fused to form agglomerates, and the particles tend to adhere to the inside of a reaction vessel. As the result, troubles are sometimes taken place such that block up or the like tends to occur when the powder is taken out from a polymerization vessel, productivity decreases or that the polymerization has to be terminated in the worst case.

On the other hand, a propylene-based block copolymer, for example, a propylene-based block copolymer consisting of a crystalline propylene copolymer part and an amorphous propylene-ethylene copolymer part (rubber part) has properties of high stiffness and excellent low temperature impact resistance, therefore, it is widely used for automobile parts, home electric appliance parts, foods field and other fields as well as general injection molding.

The propylene-based block copolymer having a high content of the rubber part exhibits excellent low temperature impact resistance, therefore, in the automobile parts field, a propylene-based block copolymer having a higher ratio of the rubber part is desired. However, since it is difficult to produce such a propylene-based block copolymer, for improving impact resistance, the method has been employed that an olefin-based elastomer such as an ethylene-propylene rubber, or a styrene-based elastomer is blended to a propylene-based block copolymer.

A propylene-based block copolymer is generally produced by homopolymerization of propylene or copolymerization of propylene with a small amount of the other α-olefin in the first process, followed by copolymerization of propylene with ethylene and/or the other α-olefin to prepare a rubber part in the second process.

The second process is frequently carried out by gas phase reaction, however, the rubber part has adhesiveness, in the production of a block copolymer, tackiness of the propylene-based block copolymer increases, and there are problems that powder particles agglutinate involved with deterioration of flowability in a polymerization vessel, and that troubles in the production tend to occur such as adhesion in the polymerization vessel and the like.

To contemplate increasing the amount of the rubber part, the above-mentioned problems get serious, and troubles such that the polymerization has to be terminated and the like are sometimes caused. Thus, the ratio of the rubber part in the production of a propylene-based block copolymer is limited under the existing circumstance.

As to the technique in order to produce propylene-based block copolymer particles containing a large amount of the rubber part, some approaches have been made.

For instance, JP-A-H9-506319 discloses a method that a crystalline polypropylene part is produced using a solid titanium catalyst component consisting magnesium, titanium and a halogen as the essential components in the first polymerization process, and an amorphous propylene-ethylene copolymer part is produced using a so-called Metallocene in the second polymerization process.

However, in this method, a step to inactivate the catalyst has to be provided after the first polymerization process, there having a defect that the processes complexity.

JP-A-2002-030128 discloses a method using a catalyst for olefin polymerization, which contains magnesium, titanium, a halogen, an electron donating compound and aluminum as the catalyst components.

However, this method cannot be said a sufficient technique to solve the problems in the production of the propylene-based block copolymer, since the technique of the solid catalyst used in this method is one similar to those of catalysts such as methods that a magnesium compound is supported on a porous inorganic oxide such as silica which is known technique (for instance, see JP-A-S63-280707), that a magnesium compound is once dissolved in a solvent such as alcohols, followed by precipitation again to obtain a catalyst (for instance, see JP-A-S58-811), and that a magnesium alkoxide compound which is obtained by reacting metal magnesium and an alcohol such as ethanol is used as a support (for instance, see JP-A-H4-130107).

From the above-mentioned back ground, a method is desired that can provide propylene-based block copolymer particles which have excellent particle flow property, from which molded articles excellent in stiffness and impact resistance can be prepared, and which can be produced with light load.

In view of the above-mentioned problems, a purpose of the present invention is to provide a magnesium compound which exhibits high activity without decrease of performances such as stereoregularity and can give an olefin polymer excellent in powder flowability and a method of production thereof, a solid catalyst component for olefin polymerization, and a catalyst for olefin polymerization.

Further, in view of the above-mentioned problems, a purpose of the present invention is to provide a propylene-based random copolymer having less tacky component, which can give a film excellent in low temperature heat sealing property and impact resistance, and a method that can stably produce the propylene-based random copolymer.

Furthermore, in view of the above-mentioned problems, a purpose of the present invention is to provide a propylene-based block copolymer having excellent particle flow property and a method of producing the same.

DISCLOSURE OF THE INVENTION

The present inventors made efforts to attain the above-mentioned purposes, as the result, they found that the above purposes can be attained by improving a magnesium compound as a support material for a solid catalyst component, and the present invention has been completed by the finding.

According to the present invention, the following magnesium compound, solid catalyst component for olefin polymerization, catalyst for olefin polymerization, and polymers can be provided.

1. A magnesium compound represented by the formula (I), $$Mg(OC_2H_5)_{2-n}(OR^1)_n \qquad (I)$$

where $R^1$ is $C_mH_{2m+1}$ (where m is an integer of from 3 to 10), and n is a numerical value satisfying $0<n<0.35$.

2. The magnesium compound according to 1, wherein n is a numerical value of from 0.005 to 0.3.

3. The magnesium compound according to 1 or 2 wherein a smoothness (Sm) represented by the expression (1) is less than 1.20:

$$Sm = (L^1/L^2)^3 \qquad (1)$$

where $L^1$ is a circumferential length of a projection view of a magnesium compound particle determined by photographing with a scanning electron microscope and thereafter an image-processing, and $L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.

4. A method of producing the magnesium compound according to any one of 1 to 3, which comprises charging and reacting the following components:
   i) metal magnesium,
   ii) ethanol,
   iii) an alcohol having from 3 to 10 carbon atoms, and
   iv) a halogen and/or a halogen-containing compound containing at least 0.0001 gram atom of a halogen atom relative to one gram of the metal magnesium
   the molar ratio of the component iii)/the component ii) being 0.001 to 0.3 in the total amount of the components ii) and iii) used.
5. The method according to 4, wherein the alcohol is n-butanol.
6. The method according to 4 or 5, wherein the halogen is iodine, and the halogen-containing compound is magnesium chloride.
7. A support for a solid catalyst component for olefin polymerization consisting essentially of the magnesium compound according to any one of 1 to 3.
8. A solid catalyst component for olefin polymerization obtained by reacting the support according to 7 with a transition metal compound.
9. The solid catalyst component for olefin polymerization according to 8, which is obtained by reacting the support with a halide and/or electron donating compound together with the transition metal compound.
10. The solid catalyst component for olefin polymerization according to 9, wherein the halide is silicon tetrachloride.
11. A catalyst for olefin polymerization comprising the following compounds (A) and (B), or the following compounds (A), (B) and (C):
   (A) the solid catalyst component for olefin polymerization according to any one of 8 to 10.
   (B) an organic aluminum compound
   (C) an electron donating compound.
12. A method of producing an olefin polymer using the catalyst for olefin polymerization according to 11.
13. A solid catalyst component for propylene-based random copolymerization obtained by reacting
   the following components (a) and (b),
   the following components (a), (b) and (c),
   the following components (a), (b) and (d), or
   the following components (a), (b), (c) and (d):
(a) a magnesium compound represented by the formula (I)

$$Mg(OC_2H_5)_{2-n}(OR^1)_n \quad (I)$$

where n is a numerical value satisfying $0<n<0.35$, $R^1$ is $C_mH_{2m+1}$, and m is an integer of from 3 to 10,
(b) a compound represented by the formula (II)

$$Ti(OR^2)_sX_{4-s} \quad (II)$$

where X is a halogen atom, $R^2$ is a hydrocarbon group having from 1 to 10 carbon atoms, a plurality of $OR^2$ groups are the same or different to each other, and s is an integer of from 0 to 4,
(c) a halide
(d) an electron donating compound.
14. The solid catalyst component for propylene-based random copolymerization according to claim 13, wherein n is a numerical value of from 0.005 to 0.3.
15. The solid catalyst component for propylene-based random copolymerization according to 13 or 14, wherein the smoothness (Sm) of the magnesium compound (a) represented by the following expression is less than 1.2:

$$Sm=(L^1/L^2)^3$$

where $L^1$ is a circumferential length of a projection view of a magnesium compound particle determined by photographing with a scanning electron microscope and thereafter an image-processing, and $L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.
16. The solid catalyst component for propylene-based random copolymerization according to any one of 13 to 15, wherein the magnesium compound (a) is a magnesium compound obtained by reacting the following components i) to iv):
   i) metal magnesium
   ii) ethanol
   iii) an alcohol having from 3 to 10 carbon atoms
   iv) a halogen and/or a halogen-containing compound containing at least 0.001 gram atom of a halogen atom relative to one gram of the metal magnesium.
17. The solid catalyst component for propylene-based random copolymerization according to 16, wherein the alcohol iii) is n-butanol.
18. The solid catalyst component for propylene-based random copolymerization according to 16 or 17, wherein the halogen iv) is iodine, and the halogen-containing compound iv) is magnesium chloride.
19. A catalyst for propylene-based random copolymerization comprising
   the following components (A), (B) and (C), or
   the following components (A) and (B):
   (A) the solid catalyst component for propylene-based random copolymerization according to any one of 13 to 18.
   (B) an organic aluminum compound
   (C) an organosilicon compound having a Si—O—C bond.
20. A method of producing a propylene-based random copolymer which comprises random copolymerizing propylene with at least one copolymerizable monomer selected from the group consisting of ethylene and α-olefins having from 4 to 20 carbon atoms, in the presence of the catalyst for propylene-based random copolymerization according to 19.
21. The method of producing a propylene-based random copolymer according to 20, wherein
   propylene or a copolymerizable monomer is brought into contact solely, or two or more monomers selected from the group consisting of propylene and copolymerizable monomers are brought into contact in the presence of the component (A), the first organic aluminum compound (B-1) and/or the first organosilicon compound (C-1), to obtain a preliminary polymerization catalyst component, and
   subsequently, propylene and a copolymerizable monomer are copolymerized in the presence of the preliminary polymerization catalyst component, the second organic aluminum compound (B-2) and the second organosilicon compound (C-2).
22. A film or sheet comprising a propylene-based random copolymer obtained by the method according to 20 or 21.
23. A solid catalyst component for propylene-based block copolymerization obtained by reacting
   the following components (a) and (b),
   the following components (a), (b) and (c),
   the following components (a), (b) and (d), or
   the following components (a), (b), (c) and (d):

(a) a magnesium compound represented by the formula (I)

$$Mg(OC_2H_5)_{2-n}(OR^1)_n \quad (I)$$

where n is a numerical value satisfying $0<n<0.35$, $R^1$ is $C_mH_{2m+1}$, and m is an integer of from 3 to 10,
(b) a compound represented by the formula (II)

$$Ti(OR^2)_sX_{4-s} \quad (II)$$

where X is a halogen atom, $R^2$ is a hydrocarbon group having from 1 to 10 carbon atoms, a plurality of $OR^2$ groups are the same or different to each other, and s is an integer of 0 to 4,
(c) a halide
(d) an electron donating compound.
24. The solid catalyst component for propylene-based block copolymerization according to 23, wherein n is a numerical value of from 0.005 to 0.3.
25. The solid catalyst component for propylene-based block copolymerization according to 23 or 24, wherein a smoothness (Sm) of the magnesium compound (a) represented by the following expression is less than 1.2:

$$Sm=(L^1/L^2)^3$$

where $L^1$ is a circumferential length of a projection view of a magnesium compound particle determined by photographing with a scanning electron microscope and thereafter an image-processing, and $L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.
26. The solid catalyst component for propylene-based block copolymerization according to any one of 23 to 25, wherein the magnesium compound (a) is a magnesium compound obtained by reacting the following components i) to iv):
  i) metal magnesium
  ii) ethanol
  iii) an alcohol having from 3 to 10 carbon atoms
  iv) a halogen and/or a halogen-containing compound containing the halogen atom in an amount of at least 0.001 gram atom relative to one gram atom of the metal magnesium.
27. The solid catalyst component for propylene-based block copolymerization according to 26, wherein the alcohol iii) is n-butanol.
28. The solid catalyst component for propylene-based block copolymerization according to 26 or 27, wherein the halogen iv) is iodine, and the halogen-containing compound iv) is magnesium chloride.
29. A catalyst for propylene-based block copolymerization comprising
  the following components (A), (B) and (C), or
  the following components (A) and (B):
(A) the solid catalyst component for propylene-based block copolymerization according to any one of 23 to 28
(B) an organic aluminum compound
(C) an electron donating compound.
30. A method of producing a propylene-based block copolymer, which comprises:
  polymerizing propylene solely or copolymerizing propylene and ethylene in the presence of the catalyst for propylene-based block copolymerization according to 29 to produce a propylene homopolymer or a propylene-based copolymer having an ethylene content of 4 weight % or below, and
  copolymerizing propylene with ethylene and/or an α-olefin having from 4 to 10 carbon atoms to produce a rubber part.
31. The method of producing a propylene-based block copolymer according to 30, wherein
  propylene or a copolymerizable monomer is brought into contact solely, or two or more monomers selected from the group consisting of propylene and copolymerizable monomers are brought into contact in the presence of the component (A), the first organic aluminum compound (B-1) and/or the first electron donating compound (C-1), to obtain a preliminary polymerization catalyst component, and
  subsequently, propylene and a copolymerizable monomer are copolymerized in the presence of the preliminary polymerization catalyst component, the second organic aluminum compound (B-2) and the second electron donating compound (C-2).
32. Propylene-based block copolymer particles, which are produced by the method according to 30 or 31, and have the following properties (i), (ii) and (iii):
(i) a ratio of normal temperature paraxylene-soluble components relative to the entire of the propylene-based block copolymer being from 5 to 60 weight %, an intrinsic viscosity [η] of the soluble component being 1 to 20 dl/g, and a ratio of the propylene constituent unit of the soluble component being from 80 to 40 weight %,
(ii) a ratio of normal temperature paraxylene-insoluble components relative to the entire of the propylene-based block copolymer being from 95 to 40 weight %, and an intrinsic viscosity [η] of the insoluble component being from 0.5 to 2.0 dl/g, and
(iii) the flowability FA (ml/sec.) which represents a flow property of the particles satisfying $$FA>100-1.8\times A/B$$

where the amount of the normal temperature paraxylene-soluble components is A (weight %), and the intrinsic viscosity [η] of the normal temperature paraxylene-soluble components is B (dl/g).

The present invention can provide a magnesium compound which exhibits high activity without deterioration of the performance such as stereoregularity and gives an olefin polymer excellent in the powder flowability and a method of producing the same, and solid catalyst component for olefin polymerization and a catalyst for olefin polymerization.

The present invention can provide a propylene-based random copolymer from which a film having less amount of the sticky component, and excellent in low-temperature heat sealing property and impact resistance can be prepared.

The present invention can provide a propylene-based block copolymer having excellent flow property of the particles, and a method of producing the same.

According to the present invention, propylene-based block copolymer particles excellent in flow property can be produced by the use of a solid catalyst using a magnesium compound prepared under the specific conditions as a basic support, and it becomes possible to stably provide in good efficiency the propylene-based block copolymer excellent in stiffness and impact resistance, which is useful for the fields such as automobile parts, home electric appliances and uses for foods.

BEST MODE FOR CARRYING OUT THE INVENTION

Figure 1:
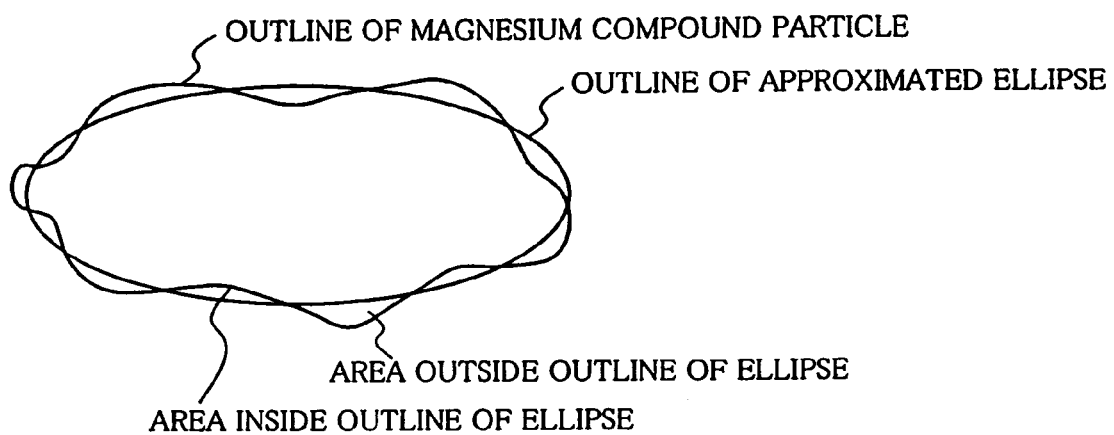
FIG. 1 is a drawing which shows one example of the ellipse approximated to the magnesium compound particle of the present invention.
Figure 2:
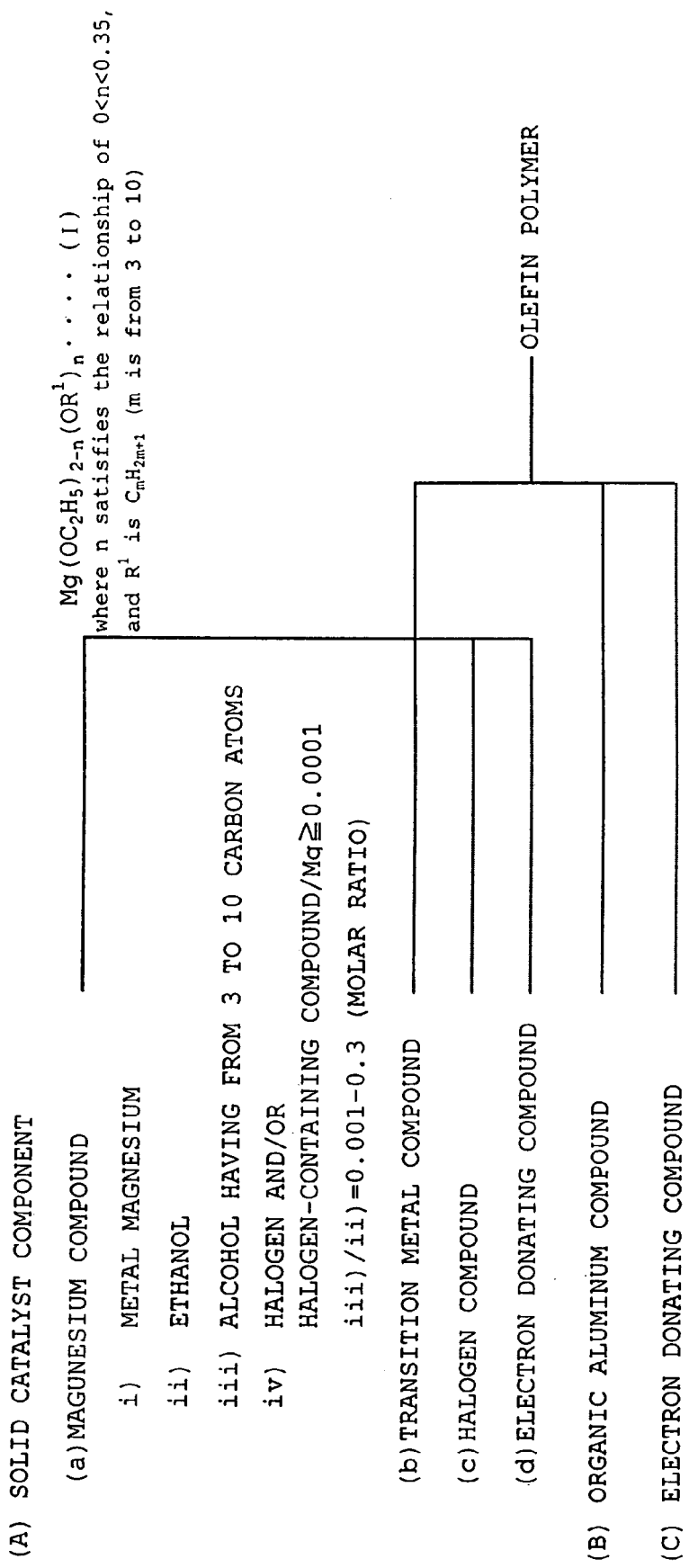
FIG. 2 is a drawing which shows the magnesium compound and the method of producing the same, the solid catalyst component for olefin polymerization, catalyst for olefin polymerization, and the method of producing olefin polymer of the present invention.
Figure 3:
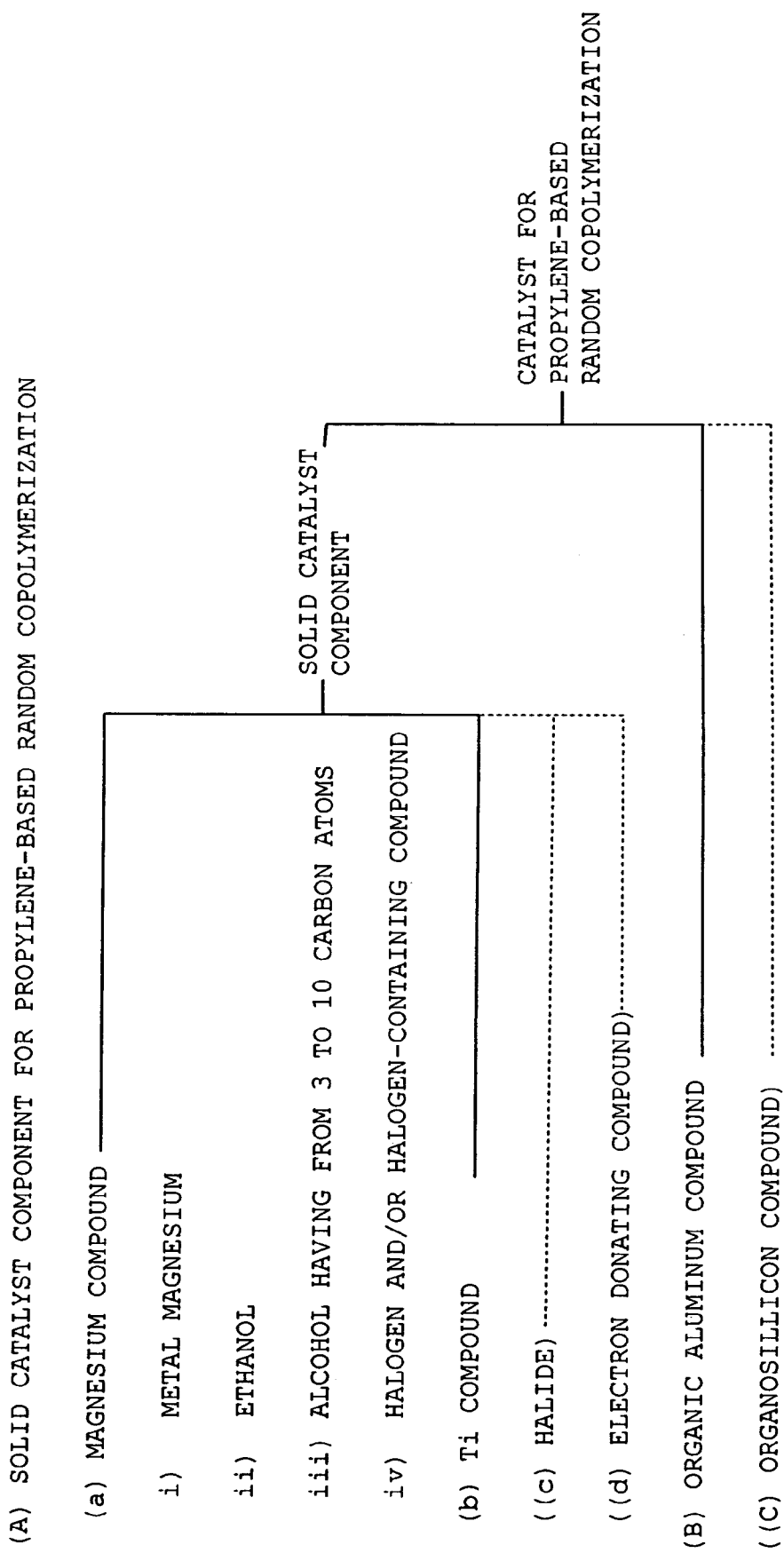
FIG. 3 is a drawing which shows the catalyst used for the production of the propylene-based random copolymer of the present invention.
Figure 4:
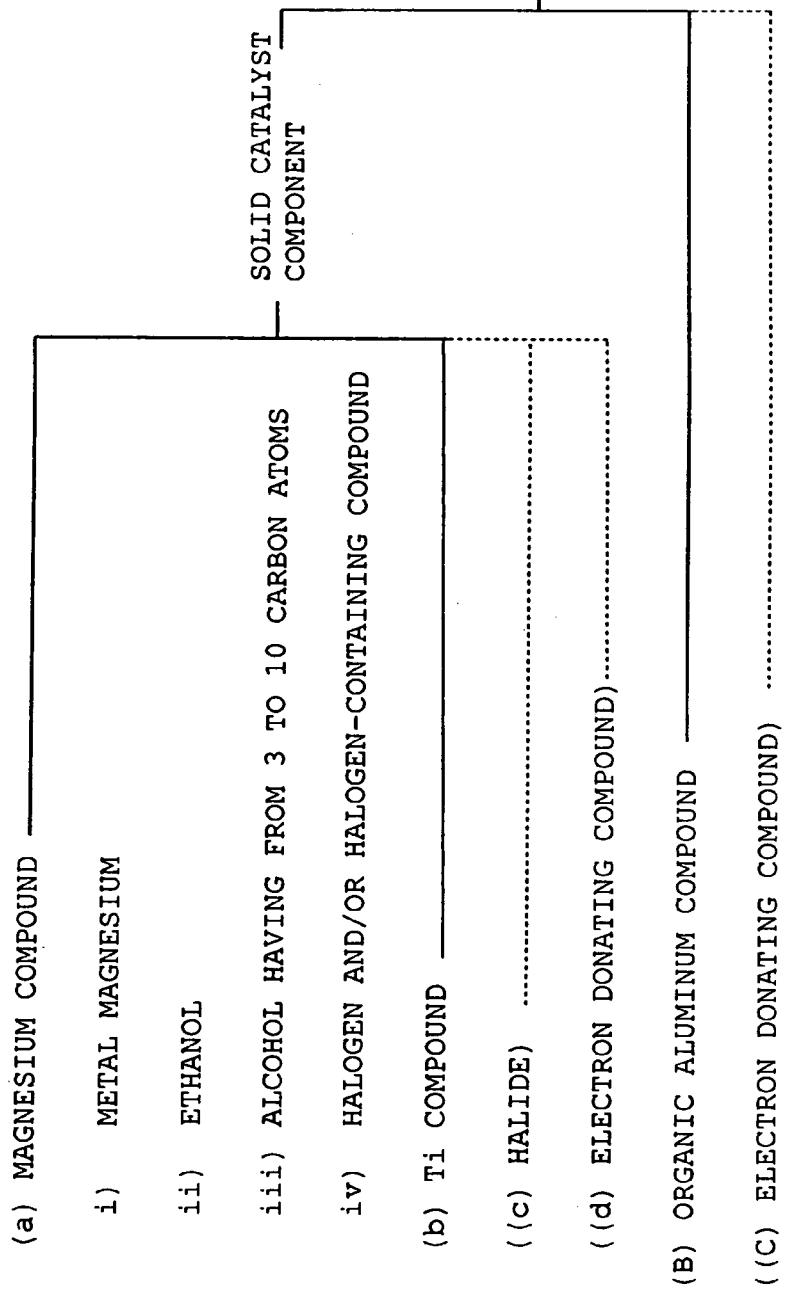
FIG. 4 is a drawing which shows the catalyst used for the production of the propylene-based block copolymer of the present invention.

The solid catalyst component (A) of the present invention contains magnesium, a transition metal, and if necessary, a halogen compound and/or an electron donating compound, and is obtained by reacting the following (a) a magnesium compound, (b) a transition metal compound, and if necessary, (c) a halogen compound and/or (d) an electron donating compound.

The method of producing olefin polymer of the present invention is characterized by the use of a catalyst for polymerization which contains (A) solid catalyst component, (B) organic metal component, and if necessary, (C) electron donating compound.

In the method of producing propylene-based random copolymer of the present invention, particularly an organosilicon compound having a Si—O—C bond is used as (C) electron donating compound.

Now, the catalyst components, method of preparing them, method of polymerization and the like will be explained, respectively.

[I] Respective Catalyst Components
(A) Solid Catalyst Components
(a) Magnesium Compound The magnesium compound (a) is represented by the formula (I). This compound is in a solid state.

$$Mg(OC_2H_5)_{2-n}(OR^1)_n \quad (I)$$

where $R^1$ is $C_mH_{2m+1}$ (where m is an integer of 3 to 10) and n is a numerical value satisfying 0<n<0.35.

In the present invention, the magnesium compound (a) is used as a support for the solid catalyst component for olefin polymerization (A). The support may substantially consist of the magnesium compound (a) of the formula (I).

Here, the term "substantially" means that not only the case where the support consists purely of the magnesium compound of $Mg(OC_2H_5)_{2-n}(OR^1)_n$ but also the case where the support additionally contains infinitesimal impurities (for instance, a case where an alcohol complex of a magnesium halide such as $MgI_2$ adheres to the support surface, which the plate crystallizations of $Mg(OC_2H_5)_{2-n}(OR^1)_n$ aggregate to let to be nearly spherical shape, and the like) are included. In the present invention, even though the impurities are contained, when the purity of $Mg(OC_2H_5)_{2-n}(OR^1)_n$ at least 95%, it can be used as the support. Preferred purity is at least 98%, more preferred purity is at least 99%.

In the formula (I), when n does not fallen within the range of 0<n<0.35, the nature of the magnesium compound approximates to that of magnesium diethoxide or a magnesium dialkoxide having from 3 to 10 carbon atoms and the desired effects are hardly exhibited, it being undesirable. Namely, when n is 0, it becomes difficult to let smoothness of the support to be less than 1.20. On the other hand, when n is not less than 0.35, the support is so soft that it is difficult to hold the support to be in the solid state. In the present invention, the composition of the magnesium compound (a) is preferably in between $Mg(OC_2H_5)_{1.995}(OR^1)_{0.005}$ and $Mg(OC_2H_5)_{1.7}(OR^1)_{0.3}$, namely n is preferably 0.005 to 0.3.

In order that n falls within a range of 0<n<0.35, in the production of the magnesium compound (a) as mentioned below, the amount ratio, alcohols having from 3 to 10 carbon atoms/ethanol may be made to 0.001 to 0.3 (molar ratio).

$R^1$ as represented by $C_mH_{2m+1}$ is preferably n-$C_3H_7$, n-$C_4H_9$, n-$C_5H_{11}$, n-$C_6H_{13}$, n-$C_7H_{15}$ and n-$C_8H_{17}$.

The smoothness (Sm) represented by the expression (1) of the magnesium compound (a) is preferably less than 1.20, more preferably less than 1.15,

$$Sm=(L^1/L^2)^3 \quad (1)$$

where $L^1$ is a circumferential length of a projection view of a magnesium compound particle determined by photographing with a scanning electron microscope and thereafter an image-processing, and $L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.

When the smoothness is 1.20 or above, flowability of the polymer powder to be obtained might be lowered.

In order to make the smoothness to be less than 1.20, in the production of the magnesium compound (a) as mentioned below, the amount ratio, alcohols having from 3 to 10 carbon atoms/ethanol may be made to 0.001 to 0.3 (molar ratio).

One example of the ellipse approximated to the magnesium compound (a) is shown in FIG. 1.

The magnesium compound (a) can be produced by reacting i) metal magnesium, ii) ethanol, iii) an alcohol having from 3 to 10 carbon atoms, and iv) a halogen and/or a halogen-containing compound containing at least 0.0001 gram atom of a halogen atom relative to the metal magnesium. Generally, the total amount of the components ii) and iii) are charged so that the molar ratio of the components iii)/ii) falls within the range of from 0.0.01 to 0.3, and reacted to produce the magnesium compound (a).

The alcohols having from 3 to 10 carbon atoms used in the present invention include n-propanol, i-propanol, n-butanol, sec-butanol, i-butanol, t-butanol, 3-methylbutanol, n-pentanol, cyclopentanol, 2-methylpentanol, 3-methylpentanol, and n-hexanol, cyclohexanol. Preferred alcohols include n-propanol, n-butanol, n-pentanol, n-hexanol, n-heptanol, and n-octanol. Particularly preferred is n-butanol.

In the present invention, although purity and water content of the ethanol and the alcohol having from 3 to 10 carbon atoms (hereinafter, these alcohols are collectively referred to as alcohols) are not particularly limited, when using alcohol having high water content, magnesium hydroxide is formed on the surface of the metal magnesium, therefore, the alcohol having water content of 1% or below, particularly 2,000 ppm or below is preferably used. Further, in order to attain better morphology, the lesser the water content is, the more preferred it is, and generally, the alcohol having water content of 200 ppm or below is desired.

Although the kinds of the halogen are not particularly limited, chlorine, bromine or iodine, particularly iodine is preferred. The kinds of the halogen-containing compound are not limited, and any compound containing a halogen atom may be used. In this case, although the kinds of the halogen atom are not particularly limited, chlorine, bromine or iodine is preferred. Among the halogen-containing compounds, halogen-containing metal compounds are particularly preferred. As the halogen-containing compound, specifically, $MgCl_2$, $MgI_2$, $Mg(OEt)Cl$, $Mg(OEt)I$, $MgBr_2$, $CaCl_2$, $NaCl$ and $KBr$ are suitably used. Of these, $MgCl_2$ is particularly preferred. The state, shape, granularity and the like of the halogen-containing compound are not particularly limited, any compound may be used, for instance, it may be used in the state of the solution in an alcohol solvent (for example, ethanol).

Although the total amount of ethanol and the alcohol having from 3 to 10 carbon atoms are not limited, it is used preferably in an amount of from 2 to 100 mole relative to one mole of the metal magnesium, particularly preferably in an amount of from 5 to 50 mole. When the total amount is too large, the yield of the magnesium compound (a) having good morphology might be reduced, and when too small, smooth agitation in the reaction vessel might not be carried out. However, it is not limited to the molar ratio mentioned above.

The amount of the halogen or the halogen-containing compound as a halogen atom per mole of the metal magnesium is 0.0001 gram atom or more, preferably 0.0005 gram atom or more, more preferably 0.001 gram atom or more. When the amount of the halogen is less than 0.0001 gram atom, there is no difference from a case where halogen is used as a reaction initiator, and when the thus-obtained magnesium compound (a) is used as a catalyst support, the catalyst may be poor in catalyst activity or an olefin polymer may be defective in morphology, and the like.

In the present invention, the halogens or the halogen-containing compounds may be used solely each, and two or more halogens or halogen-containing compounds of these may be used in combination. Further, the halogen and the halogen-containing compound may be used in combination. When the halogen and the halogen-containing compound are used in combination, the amount of total halogen atoms in the halogen and the halogen-containing compound per mole of the metal magnesium is 0.0001 gram atom or more, preferably 0.0005 gram atom or more, more preferably 0.001 gram atom or more.

While the upper limit of the amount(s) of the halogen and/or the halogen-containing compound is not specially limited, the upper limit may be set as required so long as the magnesium compound (a) for use in the present invention can be obtained. Generally, the above upper limit is preferably less than 0.06 gram atom.

In the present invention, the particle diameter of the magnesium compound (a) can freely be adjusted during the production by optionally selecting the amount of the halogen and/or halogen-containing compound used. Specifically, the average particle diameter of the magnesium compound (a) can optionally be varied depending upon the kind of olefin polymerization process, the kind of the solid catalyst component or the like.

The average particle diameter of the magnesium compound (a) is preferably from 10 to 80 μm, and to specifically indicate it depending upon the propylene polymerization process, the average particle diameters are as follows:

In the case of Spheripol type process: from 30 to 50 μm
In the case of Unipol type process: from 10 to 20 μm
In the case of Novolen type process: from 30 to 60 μm
In the case of Hypol type process: from 10 to 20 μm In the production of the magnesium compound (a) the metal magnesium, ethanol, an alcohol having from 3 to 10 carbon atoms, and the halogen and/or halogen-containing compound are reacted (usually for 10 to 30 hours) until hydrogen gas generation terminates. Specifically, the magnesium compound (a) can be produced by the process when using iodine as the halogen, such that iodine in a solid state is added into the alcohol solution of the metal magnesium, and then, followed by reaction with heat; that the alcohol solution of iodine is dropwise added to the alcohol solution of the metal magnesium, followed by reaction with heat; or that while heating the alcohol solution of the metal magnesium, the alcohol solution of iodine is dropwise added to the alcohol solution of the metal magnesium, followed by reaction.

Each method is preferably carried out in the atmosphere of an inert gas (e.g., nitrogen gas or argon gas) and optionally in the presence of an inert organic solvent (e.g., saturated hydrocarbon such as n-hexane).

Further, it is not required to charge the entire amount of each of the metal magnesium, the alcohol and the halogen at once from the beginning, and they may be divided and partially charged. In a particularly preferred embodiment, the alcohol is entirely charged in the beginning, the metal magnesium is divided into several portions and such portions are charged separately. In this embodiment, the generation of a large amount of hydrogen gas can be prevented, which is desirable in view of safety. Further, the size of a reaction vessel can be decreased. Further, it is also made possible to prevent the dissipation of alcohol and halogen caused by the momentary generation of a large amount of hydrogen gas. While the number of the divisional portions can be determined by taking account of the size of the reaction vessel and is not specially limited, suitably, each is generally divided into five to ten portions in view of complicatedness of procedures.

Further, the reaction may be carried out by any one of a batch method and a continuous method. Further, there may be employed a variant method in which the entire amount of the alcohol is charged in the beginning, a small amount of the metal magnesium is added to the alcohol, a product formed by a reaction is removed by separating it into other vessel, then, a small amount of the metal magnesium is charged, and these procedures are repeated.

When using the thus-obtained magnesium compound (a) for the production of the solid catalyst component (A), dried one or one washed with an inert solvent such as heptane after filtration may be used.

In each case, the magnesium compound (a) used for the present invention can be used in the following steps without subjecting to pulverization or classify manipulation for uniforming the particle size distribution. Further, the magnesium compound (a) has a shape near to a sphere, a sharp particle size distribution and the small sphericity variation of each particle.

The magnesium compound (a) may be used solely, or in combination of two kinds or more. Further, it may be used in the state of supported on a support such as silica, alumina or polystyrene, and as a mixture with a halogen or the like.

(b) Transition Metal Compound

The transition metal compound (b) used in the present invention is not limited so long as it is used as a known transition metal catalyst component for olefin polymerization such as Ziegler-Natta catalysts, metallocen catalysts, and other catalysts.

In the present invention, as the transition metal component, the titanium compound represented by the following formula (II) may preferably be used,

$$Ti(OR)_s X_{4-s} \qquad (II)$$

where X is a halogen atom, $R^2$ is a hydrocarbon group having from 1 to 10 carbon atoms, plural $OR^2$ are the same or different to each other, and s is an integer of from 0 to 4.

In the formula (II), X denotes a halogen atom, and of halogen atoms, preferred is a chlorine atom or a bromine atom and particularly preferred is a chlorine atom.

$R^2$ denotes a hydrocarbon group, which may be a saturated group or an unsaturated group, which may have a straight chain, branched chain or cyclic structure. As $R^2$, an alkyl group, an alkenyl group, a cycloalkenyl group, an aryl group and an aralkyl group are particularly preferred, and a straight chain or branched chain alkyl group is particularly preferred. When a plurality of groups as —OR are present, one of these may be the same as, or different from, the other or every other one. Specific examples of $R^2$ include methyl, ethyl, n-propyl, isopropyl, n-butyl, sec-butyl, isobutyl, n-pentyl, n-hexyl, n-heptyl, n-octyl, n-decyl, allyl, butenyl, cyclopentyl, cyclohexyl, cyclohexenyl, phenyl, tolyl, benzyl and phenethyl. is preferably an integer of from 0 to 2, and more preferably from 0 to 1.

Specific examples of the halogen-containing titanium compounds of the above general formula (II) include tetraalkoxy titanium such as tetramethoxytitanium, tetraethoxytitanium, tetra-n-propoxytitanium, tatraisopropoxytitanium, tetra-n-butoxytitanium, tetraisobutoxytitanium, tetracyclohexyloxytitanium, and tetraphenoxytitanium; titanium tetrahalides such as titanium tetrachloride, titanium tetrabromide and titanium tetraiodide; alkoxytitanium trihalides such as methoxytitanium trichloride, ethoxytitanium trichloride, propoxytitanium trichloride, n-butoxytitanium trichloride and ethoxytitanium tribromide; dialkoxytitanium dihalides such as dimethoxytitanium dichloride, diethoxytitanium dichloride, diisopropoxytitanium dichloride, di-n-propoxytitanium dichloride and diethoxytitanium dibromide; and trialkoxytitanium monohalides such as trimethoxytitanium chloride, triethoxytitanium chloride, triisopropoxytitanium chloride, tri-n-propoxytitanium chloride and tri-n-butoxytitanium chloride. Of these, high-halogenated titanium compounds are preferred, and titanium tetrachloride is particularly preferred, in view of polymerization activity. These halogen-containing titanium compounds may be used solely, or two or more compounds of these may be used in combination.

(c) Halide

The halide includes silicon tetrachloride, silicon tetrabromide, tin tetrachloride and hydrogen chloride, and of these, silicon tetrachloride is particularly preferred. These halides may be used solely each, and two or more halides may be used in combination.

(d) Electron Donating Compound

In the present invention, if necessary, an electron-donating compound (d) is employed. The electron-donating compound (d) is preferably used since it may improve the stereoregularity of an olefin polymer to be obtained. The electron-donating compounds (d) include oxygen-containing compounds such as alcohols, phenols, ketones, aldehydes, carboxylic acids, malonic acids, esters of organic acids or inorganic acids and ethers such as monoether, diether and polyether, and nitrogen-containing compounds such as ammonia, amine, nitrile and isocyanate. Of these, esters of polycarboxylic acids are preferred, and esters of aromatic polycarboxylic acids are more preferred. Of these, a monoester and/or a diester of aromatic dicarboxylic acid are/is particularly preferred in view of polymerization activity. Further, the organic groups of the ester portions are preferably a linear, branched or cyclic aliphatic hydrocarbon group.

Specific examples of the electron-donating compounds include dialkyl esters such as methyl, ethyl, n-propyl, isopropyl, n-butyl, isobutyl, t-butyl, n-pentyl, 1-methylbutyl, 2-methylbutyl, 3-methylbutyl, 1,1-dimethylpropyl, 1-methylpentyl, 2-methylpentyl, 3-methylpentyl, 4-methylpentyl, 1-ethylbutyl, 2-ethylbutyl, n-hexyl, cyclohexyl, n-heptyl, n-octyl, n-nonyl, 2-methylhexyl, 3-methylhexyl, 4-methylhexyl, 2-ethylhexyl, 3-ethylhexyl, 4-ethylhexyl, 2-methylpentyl, 3-methylpentyl, 2-ethylpentyl or 3-ethylpentyl dicarboxylates such as phthalate, naphthalene-1,2-dicarboxylate, naphthalene-2,3-dicarboxylate, 5,6,7,8-tetrahydronaphthalene-1,2-dicarboxylate, 5,6,7,8-tetrahydronaphthalene-2,3-dicarboxylate, indan-4,5-dicarboxylate and indan-5,6-dicarboxylate. Of these, phthalic acid diesters are preferred, and phthalic acid diesters in which the organic group of an ester portion is a linear or branched aliphatic hydrocarbon group having 4 or more carbon atoms are particularly preferred.

Preferable specific examples thereof include di-n-butyl phthalate, diisobutyl phthalate, di-n-heptyl phthalate and diethyl phthalate and the like. These electron-donating compounds (d) may be used solely each, or two or more thereof may be used in combination.

(B) Organic Aluminum Compound

Although not specially limited, the organic aluminum compound (B) can be preferably selected from an organic aluminum compound having an alkyl group, a halogen atom, a hydrogen atom and an alkoxy group, aluminoxane, or a mixture of these. Specific examples thereof include trialkylaluminum compounds such as trimethylaluminum, triethylaluminum, triisopropylaluminum, triisobutylaluminum and trioctylaluminum; dialkylaluminum monochlorides such as diethylaluminum monochloride, diisopropylaluminum monochloride, diisobutylaluminum monochloride and dioctylaluminum monochloride; alkylaluminum sesquihalides such as ethylaluminum sesquichloride; and linear aluminoxanes such as methylaluminoxane. Of these organic aluminum compounds, trialkylaluminum having a lower alkyl group having 1 to 5 carbon atoms is preferred, and trimethylaluminum, triethylaluminum, tripropylaluminum and triisobutylaluminum are particularly preferred. These organic aluminum compounds (B) may be used solely, or two or more thereof may be used in combination.

The organic aluminum compound used for regular polymerization may be the same to or different from the organic aluminum compound used for preliminary polymerization.

(C) Electron Donating Compound

In the present invention, if necessary as the third component, an electron donating compound (C) is used (in the case of random copolymer, an organosilicon compound having a Si—O—C bond as the electron donating compound (C) is used). The electron-donating compound (C) is preferably used since it may improve the stereoregularity of an olefin polymer to be obtained.

As the electron donating compound, organosilicon compounds having an alkoxy group, nitrogen-containing compounds, phosphorous-containing compounds and oxygen-containing compounds may be used. Of these, it is particularly preferred to use an organosilicon compound having an alkoxy group.

Specific examples of the organosilicon compound having an alkoxy group (the organosilicon compound having a Si—O—C bond) include trimethylmethoxysilane, trimethylethoxysilane, triethylmethoxysilane, triethylethoxysilane, dimethyldimethoxysilane, dimethyldiethoxysilane, ethylisopropyldimethoxysilane, propylisopropyldimethoxysilane, diisopropyldimethoxysilane, diisobutyldimethoxysilane, isopropylisobutyldimethoxysilane, di-t-butyldimethoxysilane, t-butylmethyldimethoxysilane, t-butylethyldimethoxysilane, t-butylpropyldimethoxysilane, t-butylisopropyldimethoxysilane, t-butylbutyldimethoxysilane, t-butylisobutyldimethoxysilane, t-butyl(s-butyl)dimethoxysilane, t-butylamyldimethoxysilane, t-butylhexyldimethoxysilane, t-butylheptyldimethoxysilane, t-butyloctyldimethoxysilane, t-butylnonyldimethoxysilane, t-butyldecyldimethoxysilane, t-butyl(3,3,3-trifluoromethylpropyl)dimethoxysilane, cyclohexylmethyldimethoxysilane, cyclohexylethyldimethoxysilane, cyclohexylpropyldimethoxysilane, cyclohexylisobutyldimethoxysilane, dimethoxysilane, dicyclohexyldimethoxysilane, cyclohexyl-t-butyldimethoxysilane, cyclopentylmethyldimethoxysilane, cyclopentylethyldimethoxysilane, cyclopentylpropyldimethoxysilane, cyclopentyl-t-butyldimethoxysilane, dicyclopentyldimethoxysilane, cyclopentylcyclohexyldimethoxysilane, bis(2-methylcyclopentyl) dimethoxysilane, bis(2,3-dimethylcyclopentyl) dimethoxysilane, α-naphthyl-1,1,2-trimethylpropyldimethoxysilane, n-tetradecanyl-1,1,2-trimethylpropyldimethoxysilane, 1,1,2-trimethylpropylmethyldimethoxysilane, 1,1,2-trimethylpropylethyldimethoxysilane, 1,1,2-trimethylpropylisopropyldimethoxysilane, 1,1,2-trimethylpropylcyclopentyldimethoxysilane, 1,1,2-trimethylpropylcyclohexyldimethoxysilane, 1,1,2-trimethylpropylmyristyldimethoxysilane, diphenyldimethoxysilane, diphenyldiethoxysilane, phenyltriethoxysilane, methyltrimethoxysilane, methyltriethoxysilane, ethyltrimethoxysilane, ethyltriethoxysilane, propyltrimethoxysilane, isopropyltrimethoxysilane, butyltrimethoxysilane, butyltriethoxysilane, isobutyltrimethoxysilane, t-butyltrimethoxysilane, s-butyltrimethoxysilane, amyltrimethoxysilane, isoamyltrimethoxysilane, cyclopentyltrimethoxysilane, cyclohexyl trimethoxysilane, norbornanetrimethoxysilane, indenyl trimethoxysilane, 2-methylcyclopentyl trimethoxysilane, ethyltriisopropoxysilane, methylcyclopentyl(t-butoxy)dimethoxysilane, isopropyl(t-butoxy)dimethoxysilane, t-butyl(t-butoxy)dimethoxysilane, (isobutoxy)dimethoxysilane, vinyltriethoxysilane, vinyltributoxysilane, chlorotriethoxysilane, γ-chloropropyltrimethoxysilane, γ-aminopropyltriethoxysilane, 1,1,2-trimethylpropyltrimethoxysilane, 1,1,2-trimethylpropylisopropoxydimethoxysilane, 1,1,2-trimethylpropyl(t-butoxy) dimethoxysilane, tetramethoxysilane, tetraethoxysilane, tetrabutoxysilane, tetraisobutoxysilane, ethyl silicate, butyl silicate, trimethylphenoxysilane, methyltriallyloxysilane, vinyltris(β-methoxyethoxy)silane, vinyltrisacetoxysilane and dimethyltetraethoxydisiloxane and the like. These organosilicon compounds may be used solely each, or two or more thereof may be used in combination.

Further, the above organosilicon compound also includes a compound obtained by reacting a silicon compound having no Si—O—C bond with an organic compound having an O—C bond in advance or by reacting these compounds during the polymerization of an α-olefin. Specifically, a compound obtained by reacting silicon tetrachloride and an alcohol is included.

Specific examples of the nitrogen-containing compound include 2,6-substituted piperidines such as 2,6-diisopropylpiperidine, 2,6-diisopropyl-4-methylpiperidine and N-methyl-2,2,6,6-tetramethylpiperidine; 2,5-substituted azolidines such as 2,5-diisopropylazolidine and N-methyl-2,2,5,5-tetramethylazolidine; substituted methylenediamines such as N,N,N',N'-tetramethylmethylenediamine and N,N,N',N'-tetraethylmethylenediamine; and substituted imidazolidines such as 1,3-dibenzylimidazolidine and 1,3-dibenzyl-2-phenylimidazolidine.

Specific examples of the phosphorus-containing compound include phosphorous acid esters such as triethyl phosphite, tri-n-propyl phosphite, triisopropyl phosphite, tri-n-butyl phosphite, triisobutyl phosphite, diethyl-n-butyl phosphite and diethylphenyl phosphite. Specific examples of the oxygen-containing compound include 2,6-substituted tetrahydrofurans such as 2,2,6,6-tetramethyltetrahydrofuran and 2,2,6,6-tetraethyltetrahydrofuran; and dimethoxymethane derivatives such as 1,1-dimethoxy-2,3,4,5-tetrachlorocyclopentadiene, 9,9-dimethoxyfluorene and diphenyldimethoxymethane.

Specific examples of the oxygen-containing compound include 2,5-substituted tetrahydrofurans such as 2,2,5,5-tetramethyltetrahydrofuran and 2,2,5,5-tetraethyltetrahydrofuran; and dimethoxymethane derivatives such as 1,1-dimethoxy-2,3,4,5-tetrachlorocyclopentadiene, 9,9-dimethoxyfluorene and diphenyldimethoxymethane.

The electron donating compound used for regular polymerization may be the same to or different from the electron donating compound used for preliminary polymerization.

[II] Preparation of Solid Catalyst Component

As a method of preparing the solid catalyst component (A), the above-mentioned magnesium compound (a), transition metal compound (titanium compound) (b) and if necessary, the halide (c) and the electron donating compound (d) may be brought into contact and react with each other.

For instance, the magnesium compound (a), the transition metal compound (titanium compound) (b), the halide (c) and the electron donating compound (d) are brought into contact at a temperature of from 120 to 150° C., and then, washed with an inert solvent at a temperature of from 100 to 150° C.

Further, these compounds are preferably brought into contact and react with each other in the amounts thereof under the condition with the operations as follows:

The transition metal compound (titanium compound) (b) is usually used in an amount within a range of from 0.5 to 100 mols relative to one mol of magnesium of the magnesium compound (a), preferably from 1 to 50 mols. Also, the electron donating compound (d) is usually used in an amount within a range of from 0.01 to 10 mols relative to one mol of magnesium of the magnesium compound (a), preferably from 0.05 to 0.15 mol. Further, as the halide (c), silicon tetrachloride is particularly preferred, and usually used in an amount within a range of from 0.01 to 10 mols relative to one mol of magnesium of the magnesium compound (a), preferably from 0.05 to 2 mols.

In the preparation of the solid catalyst component, after addition of the above-mentioned compounds (a), (b) and (d), or after addition of the above-mentioned compounds (a), (b), (c) and (d), they are preferably brought into contact with each other usually at a temperature within a range of from −20 to 200° C., preferably from 120 to 150° C., and more preferably from 125 to 140° C. When the contact temperature is outside the above-mentioned range, the catalyst activity or the propylene-based random copolymer having desired resin properties might not be obtained.

The contact period of time at the above-mentioned range of temperature is usually from one minute to 24 hours, preferably from 10 minutes to 6 hours. The procedure of the contact operation is not limited. For instance, the components may be previously brought into contact with each other in the presence of an inert solvent such as hydrocarbon, or the components previously diluted with an inert solvent such as hydrocarbon may be brought into contact with each other. The inert solvent includes aliphatic hydrocarbons such as n-pentane, isopentane, n-hexane, n-heptane, n-octane and isooctane; aromatic hydrocarbons such as benzene, toluene and xylene, and the mixture of these hydrocarbons. Although pressure at this time, when using the solvent, varies its range depending upon the kinds of the solvent, the contact temperature and the like, and the contact is usually within a range of from 0 to 50 kg/cm$^2$G, preferably from 0 to 10 kg/cm$^2$G. Further, during the contact operation, stirring is preferably carried out from the viewpoint of the uniformity of contact and the contact efficiency.

Furthermore, the contact of the transition metal compound (titanium compound) is preferably carried out two or more times so that the transition metal compound is sufficiently supported on the magnesium compound which serves as the catalyst support. When using a solvent in the contact procedure, the solvent is usually used in an amount of 5,000 mL or less relative to one mol of the transition metal compound (titanium compound), preferably from 10 to 1,000 mL. When the ratio of the solvent deviates from the above-mentioned range, the uniformity of contact or contact efficiency might deteriorate.

The solid catalyst component obtained by the above-mentioned contact procedure is washed with an inert solvent at a temperature of from 100 to 150° C., preferably from 120 to 140° C. When the washing temperature is outside the above-mentioned range, the desired catalyst activity or resin properties might not be obtained. The inert solvent includes aliphatic hydrocarbons such as octane and decane, alicyclic hydrocarbons such as methylcyclohexane and ethylcyclohexane, aromatic hydrocarbons such as toluene and xylene, halogenated hydrocarbon such as tetrachloroethane and chlorfluorocarbons, and mixtures thereof. Of these, aliphatic hydrocarbons are preferably used.

Although the washing method is not particularly limited, methods such as decantation and filtration are preferred. Although the amount of the inert solvent used, washing period of time and number of washing times are also not particularly limited, the solvent is usually used in an amount of from 100 to 100,000 mL, preferably from 1,000 to 50,000 mL relative to one mol of the magnesium compound (a) per one washing operation, and the contact is usually carried out for one minute to 24 hours, preferably fro 10 minutes to 6 hours. When the ratio of the solvent is outside the above-mentioned range, the washing might not be carried out in complete manner.

Although pressure at this time varies its range depending upon the kind of solvent, the washing temperature and the like, the washing is usually carried out under a pressure within a range of from 0 to 50 kg/cm$^2$G, preferably from 0 to 10 kg/cm$^2$G. Further, during the washing operation, stirring is preferably carried out from the viewpoint of the uniformity of washing and the washing efficiency. Furthermore, it is efficient to repeat the washing operation preferably 5 times or more. The solid catalyst component thus obtained can be stored in the dried state, or in an inert solvent such as hydrocarbons.

[III] Polymerization

Although the amount of each component of the catalyst in the present invention is not especially limited, the solid catalyst component (A) is used in such an amount that the titanium atom amount per liter of a reaction volume is generally in the range of 0.00005 to 1 mmol.

The organic aluminum compound (B) is used in such an amount that the aluminum/titanium atomic ratio is generally in the range of from 1 to 10,000, preferably from 1 to 5,000, more preferably from 10 to 2,000. When the above atomic ratio is outside the above-mentioned range, the catalyst activity is sometimes insufficient. Further, the organosilicon compound (C) is used in such an amount that the electron donating compound (C)/the organic aluminum compound (B) molar ratio is generally in the range of from 0.001 to 5.0, preferably from 0.01 to 2.0, more preferably from 0.02 to 1.0, particularly preferably from 0.05 to 1.0. When the above molar ratio is outside the above range, the sufficient catalyst activity and the desired resin structure sometimes cannot be obtained. When a preliminary polymerization is carried out, however, the amount of the organosilicon compound (C) can be further decreased.

By the use of the above-mentioned catalyst, an olefin, preferably α-olefin having from 2 to 20 carbon atoms can be polymerized. The polymerization includes homopolymerization and copolymerization.

In the method of producing the propylene-based random copolymer or the propylene-based block copolymer of the present invention, propylene and at least one copolymerizable monomer selected from the group consisting of ethylene and α-olefins having from 4 to 20 carbon atoms are copolymerized.

The α-olefin having from 4 to 20 carbon atoms used in the present invention is preferably the one represented by the following formula (IV):

$$R^3\text{—CH}=\text{CH}_2 \qquad (IV)$$

In the formula (IV), $R^3$ is a hydrocarbon group having from 2 to 18 carbon atoms, and the hydrocarbon group may be saturated or unsaturated, may be linear or branched, or may be cyclic. Specific examples of the α-olefin include 1-butene, 1-pentene, 1-hexene, 1-heptene, 1-octene, 1-decene, 3-methyl-1-pentene, 4-methyl-1-pentene, vinylcyclohexane, butadiene, isoprene, piperylene, and the like.

The copolymerizable monomer includes ethylene, 1-butene, 1-pentene, 1-hexene, 1-heptene, 1-octene and 1-decene, and particularly preferred are ethylene and 1-butene.

In the polymerization of an olefin in the present invention, the preliminary polymerization of an olefin may be carried out as required before the regular polymerization thereof in view of the polymerization activity, the stereoregularity and power form of an olefin polymer. In this case, the preliminary polymerization of an olefin is carried out in the presence of a catalyst that is a mixture of predetermined amounts of the solid catalyst component (A), the first aluminum compound (B-1) and optionally the first organosilicon compound (C-1) generally in the temperature range of from 0 to 100° C. under a pressure of from atmospheric pressure to approximately 5 MPa, and then the regular polymerization of the olefin is carried out in the presence of the catalyst and the preliminary polymerization product.

In the propylene-based random copolymerization or block copolymerization by the present invention, propylene and a copolymerizable monomer solely or two or more thereof are mixed and polymerized in the presence of the catalyst generally at a temperature range of 80° C. or below, preferably from −10° C. to 60° C., more preferably from 0° C. to 50° C., under preferably a pressure of from atmospheric pressure to approximately 5 MPa.

The amount of the monomers to be preliminary polymerized is preferably from 0.05 to 50 g, more preferably from 0.1 to 10 g per one gram of the above-mentioned solid catalyst component (A). The mode of the preliminary polymerization may be a batch-wise or continuous manner.

After the preliminary polymerization, the preliminary polymerization catalyst component, in the presence of the second organic aluminum compound (B-2) and the second organosilicon compound (C-2), an olefin or propylene is copolymerized with a copolymerizable monomer to conduct the regular polymerization.

The first organic aluminum compound (B-1) and the first organosilicon compound (C-1) used in the preliminary polymerization may be the same as or different from the second organic aluminum compound (B-2) and the second organosilicon compound (C-2) used in the regular polymerization.

The polymerization type of the regular polymerization is not especially limited. Further, any one of a batch polymerization and a continuous polymerization can be employed, and there can be employed two-step polymerization or multi-step polymerization that is carried out under different conditions.

The polymerization condition is not especially limited, the polymerization pressure therefor (in the case of a block copolymer, both the first process polymerization part and the second process polymerization part are involved) is optionally selected within a pressure range of generally from atmospheric pressure to 8 MPa (Gauge), preferably from 0.2 to 5 MPa (Gauge) and the polymerization temperature is optionally selected within a temperature range of generally from 0 to 200° C., preferably from 30 to 100° C. Although the polymerization time period varies depending upon the ratio of raw materials of propylene, ethylene and the other olefins or the polymerization temperature so that it cannot be categorically determined, it is generally from 5 minutes to 20 hours, preferably approximately from 10 minutes to 10 hours. The molecular weight of the copolymer can be adjusted by the addition of a chain transfer agent, preferably the addition of hydrogen. Further, an inert gas such as nitrogen may be existed. Further, an amount supplied of the copolymerizable monomer is adjusted such that the content of the copolymerizable monomer unit in the copolymer agrees with the desired value.

Alternatively, after the catalyst components (A) (B) and (C) used in the present invention are mixed in the predetermined ratio and brought into contact, monomers (olefin, or propylene or propylene and a copolymerizable monomer) may be charged to polymerization at once, or the catalyst components are subjected to maturation for approximately from 0.2 to 3 hours after contact operation, then, monomers (olefin, or propylene or propylene and a copolymerizable monomer) may be charged to polymerization. Further, the catalyst components can be supplied in the state of a suspension in an inert solvent, propylene or the like.

As the preferred method of producing a block copolymer, first, propylene is polymerized, or propylene and ethylene are copolymerized in the first process to produce a propylene homopolymer particles, or a propylene-based copolymer particles having ethylene content of 4 weight % or less, followed by copolymerization of propylene with ethylene and/or an α-olefin having from 4 to 10 carbon atoms to produce a rubber portion in the second process. Although number of polymerization times in the first and second processes are especially limited, generally, polymerization is carried out in a range of from 1 to 7 steps in the first process, and in a range of from 1 to 3 steps in the second process.

For instance, in the case of the production through a continuous polymerization method, raw material propylene gas and hydrogen gas as a molecular weight regulant and a catalyst are supplied to a polymerization vessel of the preliminary step to produce a propylene homopolymerized portion while controlling the amount of polymerization with polymerization time period, then, the produced polymer is transferred to a polymerization vessel of the subsequent step, and raw material propylene gas, a copolymerizable monomer, hydrogen gas, and if necessary, a catalyst and additives such as alcohols are added to produce a copolymerized portion, and a block copolymer is produced.

The polymerization type of the first process is not especially limited, and any one of slurry polymerization, gas phase polymerization, bulk polymerization, etc. can be employed, further, any one of a batch polymerization and a continuous polymerization can be employed. As the second polymerization type of the second process, gas phase polymerization is employed in usual, however, any one of slurry polymerization and bulk polymerization may be employed.

In the present invention, after-treatment of polymerization can be carried out with common procedures. Namely, in the gas phase polymerization, nitrogen gas stream may be passed through the polymer powder got off from the polymerization vessel after polymerization to remove the monomers therein, or, if necessary, the polymer may be pelletized with an extrusion machine, and in this regard, a small amount of water, an alcohol or the like may be added in order to completely deactivate the catalyst. In the bulk polymerization, the monomers may be completely separated from the polymer got off from the polymerization vessel after polymerization, followed by pelletizing of the polymer.

[IV] Propylene-Based Random Copolymer

The propylene-based random copolymer obtained by the method of producing it of the present invention has a tacky component content of 3 weight % or less, which is represented by a boiling ether-soluble content ES (weight %), it being less tacky. The propylene-based random copolymer produced by the method of the present invention has 80% or less ES in comparison with a conventional propylene-based random copolymer having a copolymerizable monomer unit content in the same as that produced by the method of the present invention therefore, it being less tacky and it can provide a film excellent in anti-blocking property. Where a propylene unit content is represented by X (weight %) the ES (weight %) and the copolymerizable monomer content (100-X)(weight %) of the propylene-based random copolymer satisfy the following relationship. When they satisfy the relationship, the propylene-based random copolymer is particularly less tacky, it being preferable.

$$ES \leq 0.6 \exp\{0.25(100-X)\}$$

When the relationship is satisfied, good anti-blocking property is elicited with a small amount of an anti-blocking agent, and a film excellent in transparency and anti-blocking property can be obtained.

The propylene unit content X of the propylene-based random copolymer obtained by the method of production of the present invention is generally in a range of from 99.5 to 94 weight %, preferably from 98 to 95 weight %. When it is less than 94 weight %, the boiling ether-soluble content ES significantly increases and tackiness increases so that problems are sometimes brought about in not only product properties but also its production. When it beyond 99.5 weight %, a film having sufficient properties might not be obtained.

The intrinsic viscosity [η] determined in tetrahydronaphthalene (tetralin solvent) at a temperature of 135° C. is generally in a range of from 1 to 4 (dl/g), preferably from 1.5 to 3.5. When it is outside from 1 to 4 (dl/g), formability at the time of forming a film sometimes deteriorates, or strength of a film sometimes decreases.

The melting point Tm (° C.) determined with a differential scanning calorimeter (DSC) and the copolymerizable monomer unit content (100-X) (weight %) of the propylene-based random copolymer preferably satisfy the following relationship.

$$Tm<160-5(100-X)$$

When the relationship is not satisfied, heat sealing property at the time of forming a film shows a tendency to be insufficient, and the anti-blocking property is sometimes lowered.

As mentioned above, the propylene-based random copolymer particles obtained by the method of production of the present invention has less amount of by-products of low molecular weight amorphous components which is represented by a boiling ether-soluble content and good flow property of the particles, therefore, in the production in a continuous gas phase reaction vessel, the amount of particles having a large diameter or agglomerates, which is formed through the particles adhering or fusion bonding to each other in the polymerization reaction vessel, no blocking up at the time of getting the particles out is brought about, and the propylene-based random copolymer particles can stably be produced. In the production thereof using a continuous slurry polymerization reaction vessel, the copolymer particles less adhere to each other and the viscosity of the polymerization system less increases, therefore, the copolymer particles can stably be produced.

When the propylene-based random copolymer of the present invention is produced by a method of production other than that of the present invention, the amount of by-product of low molecular weight amorphous components sometimes increases, or the flow property of the particles sometimes deteriorates, and in the case of the production using a continuous gas phase reaction vessel, blocking up at the time of getting the particles off tends to bring about. In the case of the production using a continuous slurry polymerization reaction vessel, adhesion or the like of the copolymer particles to each other and increase of the viscosity in the polymerization system sometimes tend to result in.

[V] Propylene-Based Block Copolymer Particle

The propylene-based block copolymer particles of the present invention can be obtained by the above-mentioned method of producing propylene-based block copolymer. The propylene-based block copolymer has an amount of which the components are soluble in normal temperature paraxylene (an amount of normal temperature paraxylene-soluble component) of from 5 to 60 weight %, preferably from 10 to 50 weight %, and intrinsic viscosity [η] of a range of from 1 to 20 (dl/g), preferably from 1.5 to 8 (dl/g) which is determined in tetrahydronaphthalene (tetralin solvent) of the normal temperature xylene-soluble component at a temperature of 135° C., and a propylene unit content in the normal temperature xylene-soluble components of a range of from 80 to 40 weight %, preferably from 75 to 50 weight %. The amount of which the components are insoluble in normal temperature paraxylene (the amount of normal xylene-insoluble components) is a range of from 95 to 40 weight %, preferably from 90 to 50 weight %, and the intrinsic viscosity [η] of the normal xylene-insoluble components is preferably from 0.5 to 2 (dl/g) determined in tetrahydronaphthalene (tetralin solvent) at a temperature of 135° C.

Further, When the amount of normal temperature xylene-soluble components of the propylene-based block copolymer particles is represented by A (weight %) and the intrinsic viscosity [η] (dl/g) of the normal temperature xylene-soluble components thereof is represented by B, flowability FA which represents flow property of the particles preferably satisfies the following relationship.

$$FA>100-1.8\times A/B$$

FA is an index representing flow property of particles, and determined by the following method.

<Method of Determining Flowability (FA)>

Sample powder is filled in a cylinder type funnel having a gate at the outlet (gate diameter of 20 mm) and an internal volume of 357 mL, thereafter the gate is opened, a time period (second) by all amount of the powder running out from the cylinder is determined, and FA is calculated by dividing the volume of the sample powder with the determined time period.

As understood from the method of determination, small FA value indicates that flow property of the particles is bad and that the particles do not flow smoothly in the polymerization vessel. In the production of the propylene-based block copolymer particles, when the particles do not flow smoothly, particularly in the case of gas phase polymerization, portions where the particles accumulate in the polymerization vessel tend to generate and the accumulated portions tend to form hot spots (portions in the polymerization vessel where the temperature is high), therefore, the particles tend to fusion bond to each other or tend to adhere to the stirring blade or inner wall of the polymerization vessel. As a result, reaction controllability in the polymerization vessel tends to deteriorate, and blocking up at the time of taking the particles off or transferring them tends to bring about or in the worst case, the operation of polymerization has to be stopped.

In general, FA of the propylene-based block copolymer particles tends to be smaller and the flowability of the particles tends to deteriorate as the rubber part content thereof increases, and when propylene-based block copolymer particles are produced using a catalyst of the conventional technique, the relationship of FA, A and B is FA<100-1.8×A/B.

When the propylene-based block copolymer particles are produced using the catalyst technique of the present invention, it is FA>100-1.8×A/B, and when the propylene-based block copolymer particles having the same rubber part content is produced, defects in the production accompanied with the above-mentioned deterioration of flowability are difficult to occur in comparison with the conventional technique, and the propylene-based block copolymer particles having high rubber part content, which cannot be produced by the conventional technique for the reason of bad flowability, can be produced.

EXAMPLES

The present invention will be specifically explained with reference Examples, while the present invention shall not be limited to Examples.

[Preparation of Magnesium Compound and Polypropylene]

In Examples and Comparative Examples, supports were measured for properties as follows.

(1) Smoothness (Sm) of Magnesium Compound

A photograph of a magnesium compound dried was taken through a scanning electron microscope (trade name: JSM-25SIII, supplied by JEOL) of 300 magnifications at an acceleration voltage of 5 KV, to obtain a negative. Then, the negative was image-processed by a transmission method. Particles equivalent to 20 pixels (one pixel being to cover a 1.389 μm×1.389 μm area) or smaller in area were cut, and the image processing was carried out with an image analyzer (supplied by Nexsus Co., Ltd.) with regard to approximately 2,000 particles remaining. In a projected view of a particle, an ellipse having an area equal to the projected area of the particle and similar to the particle was superposed on the particle, and the ellipse was approximated such that the sum total of areas inside and outside the outline of the ellipse among the areas of parts defined by the outlines of the ellipse and the particle was the smallest. Circumferential lengths $L^1$ of the particle and circumferential lengths $L^2$ of the ellipse were determined, and the smoothness was calculated on the basis of the following expression (1).

$$Sm=(L^1/L^2)^3 \quad (1)$$

where $L^1$ is a circumferential length of a projection view of a magnesium compound particle determined by photographing with a scanning electron microscope and thereafter an image-processing, and $L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.

(2) Average Particle Diameter ($D_{50}$) of Magnesium Compound

A magnesium compound was suspended in a hydrocarbon, and in this state, the magnesium compound was measured for particle diameters by a light scattering method. A particle diameter distribution determined by the measurement was plotted on a logarithmic normal probability paper, and a 50% particle diameter was taken as an average particle diameter ($D_{50}$).

$$n \text{ of } Mg(OC_2H_5)_{2-n}(OR)_n \quad (3)$$

A 1.2N hydrochloric acid aqueous solution was added to a support, the mixture was stirred at room temperature for 24 hours to decompose the support, and a corresponding alcohol amount was quantitatively determined by gas chromatography to determine n.

In Examples and Comparative Examples, polymer properties were measured by the following methods.

(1) Smoothness of Polymer Powder (Sm')

A photograph of a polymer powder was taken with a polarization microscope (trade name: BHS-751P, supplied by Olympus Corporation) of 30 magnifications and image-processed. Particles equivalent to 20 pixels (one pixel being to cover a 0.0813 mm×0.0813 mm area) or smaller in area were cut, and the image processing was carried out with an image analyzer (supplied by Nexsus Co., Ltd.) with regard to approximately 2,000 particles remaining. In a projected view of a polymer powder, an ellipse having an area equal to the projected area of the polymer powder and similar to the polymer powder was superposed on the polymer powder and the ellipse was approximated such that the sum total of areas inside and outside the outline of the ellipse among the areas of parts defined by the outlines of the ellipse and the polymer powder was the smallest. Circumferential lengths $L^3$ of the polymer powder and circumferential lengths $L^4$ of the ellipse were determined, and the smoothness was calculated on the basis of the following expression (2).

$$Sm=(L^3/L^4)^3 \quad (2)$$

where $L^3$ is a circumferential length of a projection view of a polymer powder determined by photographing with a scanning electron microscope and thereafter an image-processing, and $L^4$ is a circumferential length of an ellipse which has an area equal to the projection area of the polymer powder and which is approximated to the outline of the polymer powder such that when the polymer powder is wrapped over the ellipse, the sum of the areas inside and outside the outline of the ellipse among the sections surrounded by the outline of the polymer powder and the outline of the ellipse becomes minimum.

(2) Isotacticity [mmmm]

A polymer was dissolved in 1,2,4-trichlorobenzene, and isotacticity was determined on the basis of signals of methyl measured at 130° C. by a proton complete decoupling method using $^{13}$C-NMR (trade name: EX-400, supplied by JEOL).

An isotactic pentad fraction [mmmm] refers to an isotactic fraction in pentad units of a polypropylene molecule chain determined on the basis of $^{13}$C-NMR spectrum as proposed by A. Zambelli, et al on page 925 of the journal of Macromolecules, Vol. 6 (1973).

Further, the method of assignment of peaks of $^{13}$C-NMR spectrum was according to the assignment proposed by A. Zambelli, et al on page 687 of the journal of Macromolecules, Vol. 8 (1975).

(3) Average Particle Diameter of Polymer Powder ($D_{50}$')

Particle diameters of a polymer powder measured with standard sieves were plotted on a logarithmic normal probability paper, and a 50% particle diameter was taken as an average particle diameter ($D_{50}$').

(4) Apparent Density (AD)

Measured according to JIS K6721.

(5) Flowability (FA)

Determined on the basis of an FA measurement value/AD. FA shows a volume of a polymer powder flowing per a unit time period, and it means that the larger the value of FA is, the better the flowability of the polymer powder is.

Measured by the foregoing method.

(6) Angle of Repose

A predetermined amount of a sample was caused to drop on a disk, a measurement line was brought into line with the angle of a pile and measured for the angle with a turn table type repose angle measuring apparatus, and the angle was taken as an angle of repose.

The angle of repose means that the smaller that value thereof is, the superior the flowability of a polymer powder is.

Differences in FA and the angle of repose are indices for the flowability of a powder. When the flowability of a powder is poor, the powder stays in a polymerization vessel, and if the portion where it stays is a hot spot (high-temperature portion in the polymerization vessel), the powder may be fused thereto or may adhere to a stirring blade. As a result, a powder transfer tube is liable to be clogged, and in a worst case, it is inevitable to stop the polymerization operation.

(7) Powder Breakage Ratio

Part of a polymer powder was sampled and measured for a total mass W. The powder was classified into particles that were nearly spherical and particles that were cracked, crushed or deformed due to fusion of a plurality of powder particles, and the nearly spherical particles alone were measured for a mass $W_1$. A powder breakage ratio was calculated from these W and $W_1$ on the basis of the following expression.

Powder breakage ratio=$100(W-W_1)/W$(mass %)

Example 1

(1) Preparation of Magnesium Compound

A three-necked flask having an internal volume of 0.5 liter and having a stirrer was flushed with nitrogen, and 225 ml (3.86 mol) of dehydrated ethanol (EtOH), 11.3 ml (0.12 mol) of n-butanol (BuOH), 1.20 g (9.5 milligram atom) of iodine and 12.0 g (0.49 milligram atom) of metal magnesium were poured into the three-necked flask and allowed to react at a reflux temperature (79° C.) with stirring (350 rpm) until no hydrogen was generated from the system, to give a magnesium compound.

(2) Preparation of Solid Catalyst Component

A three-necked flask having an internal volume of 0.5 liter and having a stirrer was flushed with nitrogen, and 16 g of the magnesium compound obtained in the above (1) and 80 ml of dehydrated octane were placed in the three-necked flask. The mixture was heated to 40° C., and 2.4 ml (23 mmol) of silicon tetrachloride was added. The mixture was stirred for 20 minutes, 3.4 ml (13 mmol) of di-n-butyl phthalate was added. The resultant solution was temperature-increased up to 80° C., and 77 ml (0.70 mol) of titanium tetrachloride was dropwise added with a dropping funnel. The internal temperature was adjusted to 125° C., and the mixture was stirred for 1 hour, which was taken as a first supporting operation. Then, the reaction product was fully washed with dehydrated octane. Further, 122 ml (1.11 mol) of titanium tetrachloride was added, the internal temperature was adjusted to 125° C., and the mixture was stirred for 2 hours, which was taken as a second supporting operation. Then, the reaction mixture was fully washed with dehydrated octane, to give a solid catalyst component.

(3) Propylene Slurry Polymerization

An autoclave made of stainless steel having an internal volume of 1 liter and having a stirrer was fully dried and flushed with nitrogen, and 400 ml of dehydrated heptane was placed therein. Further, 2.0 mmol of triethylaluminum was added, then, 0.25 mmol of dicyclopentyldimethoxysilane was added, and the solid catalyst component prepared in the above (2) was added in an amount of 0.0025 mmol per Ti. Hydrogen was introduced up to 0.1 MPa, and then propylene was introduced. Polymerization was carried out for 1 hour at a total pressure of 0.8 MPa and a temperature of 80° C. Then, the temperature was decreased, the pressure was decreased, and a reaction product was taken out and poured into 2 liters of methanol and vacuum-dried to give polypropylene. Table 1 shows the results.

(4) Measurement of Breakage Ratio

A 200L-Novolen type vapor-phase continuous polymerization vessel was used. While 1.5 g/hour of the solid catalyst component prepared in the above (2), 120 mmol/hour of triethylaluminum, 34.8 mmol/hour of cyclohexylmethyldimethoxysilane(CHMDMS) and 3 normal L/kg of hydrogen/propylene were continuously fed into the polymerization vessel, continuous polymerization was carried out at 70° C. for 1.5 hours. The thus-obtained polymer powder was measured for a breakage ratio according to the above-described method to show 3 mass %.

Example 2

(1) Preparation of Magnesium Compound

Example 1(1) was repeated except that the iodine was replaced with 0.45 g (9.5 milligram atom) of anhydrous magnesium chloride.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 3

(1) Example 1(1) was repeated except that the amount of iodine was changed to 0.72 g (5.7 milligram atom) and that the number of times of the stirring was changed to 525 rpm.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 4

(1) Preparation of Magnesium Compound

Example 1(1) was repeated except that the amount of ethanol was changed to 231 ml (3.96 mol), that the amount of n-butanol was changed to 2.3 ml (25 mmol) and a reaction temperature of 78° C. was employed.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 5

(1) Preparation of Magnesium Compound

Example 1(1) was repeated except that the amount of ethanol was changed to 203 ml (3.46 mol) and that the amount of n-butanol was changed to 45.1 ml (0.49 mol).

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 6

(1) Preparation of Magnesium Compound

A magnesium compound was prepared in the same way as in Example 1 (1) under the conditions shown in Table 1.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 7

(1) Preparation of Magnesium Compound

A magnesium compound was prepared in the same way as in Example 1 (1) under the conditions shown in Table 1.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 8

(1) Preparation of Magnesium Compound

A magnesium compound was prepared in the same way as in Example 1 (1) under the conditions shown in Table 1.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 1 shows the results.

Example 9

(1) Preparation of Magnesium Compound

A magnesium compound was prepared in the same way as in Example 1 (1) under the conditions shown in Table 2.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

Example 10

(1) Preparation of Magnesium Compound

A magnesium compound was prepared in the same way as in Example 1 (1) under the conditions shown in Table 2.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

Example 11

(1) Preparation of Magnesium Compound

A magnesium compound was prepared in the same way as in Example 1 (1) under the conditions shown in Table 2.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

Example 12

(1) Preparation of Magnesium Compound

A magnesium compound was prepared in the same way as in Example 1 (1) under the conditions shown in Table 2.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

Comparative Example 1

(1) Preparation of Magnesium Compound

Example 1(1) was repeated except that no n-butanol was used, that the amount of ethanol was changed to 230 ml (3.94 mol) and that a reaction temperature of 78° C. was employed.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

(4) Measurement of Breakage Ratio

A polymer powder was obtained in the same manner as in Example 1(4) except that the solid catalyst component obtained in the above (2) was used at a rate of 1.65 g/hour. The thus-obtained polymer powder was measured for a breakage ratio according to the above-described method, to show 38 mass %.

Comparative Example 2

(1) Preparation of Magnesium Compound

A magnesium compound was prepared in the same way as in Example 1 (1) under the conditions shown in Table 2. Table 2 shows the results. Polymerization was not carried out, since the properties of the support obtained were bad.

Comparative Example 3

1) Preparation of Magnesium Compound

A magnesium compound was prepared in the same way as in Example 1 (1) under the conditions shown in Table 2. Table 2 shows the results. Polymerization was not carried out, since the properties of the support obtained were bad.

Comparative Example 4

(1) Preparation of Magnesium Compound

A magnesium compound was prepared in the same way as in Example 1 (1) under the conditions shown in Table 2.

(2) Preparation of Solid Catalyst Component

Example 1(2) was repeated except that the magnesium compound prepared in the above (1) was used in place.

(3) Propylene Polymerization

Example 1(3) was repeated except that the solid catalyst component obtained in the above (2) was used in place. Table 2 shows the results.

TABLE 1

|  |  | Unit | Example 1 | Example 2 | Example 3 | Example 4 | Example 5 | Example 6 | Example 7 | Example 8 |
|---|---|---|---|---|---|---|---|---|---|---|
| Support | EtOH/Mg | (Molar ratio) | 7.75 | 7.75 | 7.75 | 7.95 | 7.00 | 7.50 | 7.50 | 7.50 |
|  | ROH species |  | n-butanol | n-butanol | n-butanol | n-butanol | n-butanol | n-propanol | n-propanol | n-propanol |
|  | ROH/Mg | (Molar ratio) | 0.25 | 0.25 | 0.25 | 0.05 | 1.00 | 0.50 | 0.50 | 0.50 |
|  | ROH/EtOH | (Molar ratio) | 0.032 | 0.032 | 0.032 | 0.006 | 0.143 | 0.067 | 0.067 | 0.067 |
|  | n: $Mg(OEt)_{2-n}(OR)_n$ |  | 0.06 | 0.06 | 0.05 | 0.01 | 0.23 | 0.13 | 0.13 | 0.14 |
|  | Halogen and/or halogen-containing compound |  | $I_2$ | $MgCl_2$ | $I_2$ | $I_2$ | $I_2$ | $I_2$ | $MgCl_2$ | $I_2$ |
|  | Halogen and/or halogen-containing compound/Mg | (Gram atom ratio) | 0.019 | 0.019 | 0.012 | 0.019 | 0.019 | 0.019 | 0.019 | 0.012 |
|  | Reaction temperature | (° C.) | 79 | 79 | 79 | 78 | 79 | 79 | 79 | 79 |
|  | Number of rotation | (rpm) | 350 | 350 | 525 | 350 | 350 | 350 | 350 | 525 |
|  | $D_{50}$ | (μm) | 61 | 59 | 46 | 64 | 60 | 60 | 58 | 44 |
|  | Sm |  | 1.12 | 1.14 | 1.18 | 1.18 | 1.19 | 1.16 | 1.18 | 1.19 |
| Polymer | Polymerization activity | (kg/g-cat) | 16.5 | 15.8 | 19.2 | 16.2 | 16.4 | 17.8 | 17.5 | 21.0 |
|  | Tacticity ([mmmm]) | (mol %) | 98.3 | 98.2 | 98.3 | 98.4 | 98.2 | 98.4 | 98.2 | 98.3 |
|  | D50' | (μm) | 1520 | 1540 | 1200 | 1600 | 1510 | 1610 | 1580 | 1300 |
|  | AD | (g/ml) | 0.38 | 0.37 | 0.39 | 0.37 | 0.36 | 0.38 | 0.37 | 0.39 |
|  | Sm' |  | 1.10 | 1.12 | 1.15 | 1.16 | 1.18 | 1.14 | 1.16 | 1.17 |
|  | FA | (mL/s) | 122 | 120 | 121 | 120 | 118 | 120 | 118 | 119 |
|  | Angle of repose | (°) | 38 | 39 | 39 | 39 | 39 | 40 | 41 | 41 |
|  | Polymer crush ratio | (wt %) | 3 | — | — | — | — | — | — | — |

TABLE 2

|  |  | Unit | Example 9 | Example 10 | Example 11 | Example 12 | Com. Example 1 | Com. Example 2 | Com. Example 3 | Com. Example 4 |
|---|---|---|---|---|---|---|---|---|---|---|
| Support | EtOH/Mg | (Molar ratio) | 7.90 | 7.75 | 7.95 | 7.90 | 8.00 | 6.00 | 6.00 | 7.50 |
|  | ROH species |  | n-hexanol | n-hexanol | n-octanol | n-decanol | — | n-butanol | n-hexanol | n-decanol |
|  | ROH/Mg | (Molar ratio) | 0.10 | 0.25 | 0.05 | 0.10 | 0.00 | 2.00 | 2.00 | 0.50 |
|  | ROH/EtOH | (Molar ratio) | 0.013 | 0.032 | 0.006 | 0.013 | 0.000 | 0.333 | 0.333 | 0.067 |
|  | n: Mg(OEt)$_{2-n}$(OR)$_n$ |  | 0.02 | 0.05 | 0.01 | 0.01 | 0.00 | 0.45 | 0.41 | 0.01 |
|  | Halogen and/or halogen-containing compound |  | I$_2$ | I$_2$ | I$_2$ | I$_2$ | I$_2$ | I$_2$ | I$_2$ | I$_2$ |
|  | Halogen and/or halogen-containing compound/Mg | (Gram atom ratio) | 0.019 | 0.019 | 0.019 | 0.019 | 0.019 | 0.019 | 0.019 | 0.019 |
|  | Reaction temperature | (° C.) | 79 | 79 | 79 | 79 | 78 | 78 | 80 | 81 |
|  | Number of rotation | (rpm) | 350 | 350 | 350 | 350 | 350 | 350 | 350 | 350 |
|  | D$_{50}$ | (μm) | 62 | 61 | 62 | 62 | 63 | 130 | 140 | 85 |
|  | Sm |  | 1.16 | 1.15 | 1.16 | 1.16 | 1.23 | 6.75 | 6.50 | 1.89 |
| Polymer | Polymerization activity | (kg/g-cat) | 18.3 | 17.6 | 16.4 | 16.1 | 15.9 | — | — | 11.4 |
|  | Tacticity ([mmmm]) | (mol %) | 98.3 | 98.4 | 98.2 | 98.2 | 98.2 | — | — | 98.1 |
|  | D50' | (μm) | 1630 | 1620 | 1590 | 1600 | 1550 | — | — | 1700 |
|  | AD | (g/ml) | 0.37 | 0.38 | 0.38 | 0.35 | 0.32 | — | — | 0.33 |
|  | Sm' |  | 1.15 | 1.13 | 1.14 | 1.14 | 1.25 | — | — | 1.65 |
|  | FA | (mL/s) | 118 | 120 | 120 | 116 | 105 | — | — | 95 |
|  | Angle of repose | (°) | 40 | 40 | 41 | 41 | 44 | — | — | 46 |
|  | Polymer crush ratio | (wt %) | — | 5 | — | — | — | 38 | — | — |

[Polymerization of Propylene Random Copolymer]

In Examples and Comparative Examples, supports were measured for properties as follows.

(1) Smoothness of Magnesium Compound (Sm)
Measured by the foregoing method.

(2) n of Mg(OEt)$_{2-n}$(OR)$_n$
Measured by the foregoing method.

In Examples and Comparative Examples, particles were measured for properties by the following method.

(1) Average Particle Diameter of Magnesium Compound (D$_{50}$)
Measured by the foregoing method.

(2) Particles Having a Size of 4 mm or Greater
Powder was classified with a sieve having openings of 4 mm and the ratio of the weight of powder remaining on the sieve to the weight of all the powder was determined.

(3) Flowability (FA)
Measured by the foregoing method.

In Examples and Comparative Examples, resins were measured for properties by the following methods.

(1) Measurement for Ethylene Content by $^{13}$C-NMR

An ethylene unit content was determined by the following method. That is, $^{13}$C-NMR measurement shown below was carried out with regard to a sample, and a triad chain fraction (mol %) of ethylene (E) and propylene (P) was calculated from seven peak-intensities in a 35 to 21 ppm [tetramethylsilane (TMS) chemical shift standard)] region in its spectrum on the basis of the following expression.

$$fEPE=[K(T\delta\delta)/T]\times 100 fPPE=[K(T\beta\delta)/T]\times 100 fEEE=[K(S\gamma\delta)/4T+K(S\delta\delta)/2T]\times 100 fPPP=[K(T\beta\beta)/T]\times 100 fPEE=[K(S\beta\gamma)/T]\times 100 fPEP=[K(S\beta\beta)/T]\times 100$$, in which $T=K(T\delta\delta)+K(T\beta\delta)+K(S\gamma\delta)/4+K(S\delta\delta)/2+K(T\beta\beta)+K(S\beta\delta)+K(S\beta\beta)$.

wherein, for example, fEPE represents a EPE triad chain fraction (mol %) and K(Tδδ) represents an integrated intensity assigned to Tδδ carbon.

An ethylene unit content (wt %) was calculated on the basis of the following expression using the above triad chain fraction.

Ethylene unit content (wt %)=28[3fEEE+2(fPEE+fEPE)+fPPE+fPEP]×100/[28[3fEEE+2(fPEE+fEPE)+fPPE+fPEP]+42[3fPPP+2(fPPE+fPEP)+fEPE+fPEE]]

A propylene structural unit content (wt %) was determined based on a 100-ethylene unit content.

<$^{13}$C-NMR Measurement>

A sample in an amount of 220 mg was taken into an NMR sample tube, 3 ml of 1,2,4-trichlorobenzene/deuterobenzene mixture solvent (volume ratio 90/10) was added, and then, the sample tube was capped. The mixture was homogeneously dissolved at 130° C. and then subjected to $^{13}$C-NMR measurement under the following measurement conditions.

Apparatus: JNM-EX400 supplied by JEOL, pulse width: 45°, Pulse recurrence period: 4 seconds, spectral width: 20,000 Hz, measurement temperature: 130° C., number of times of integrating: 1,000-10,000 times.

(2) Intrinsic Viscosity [η]
Measured in α-tetralin solvent with a VMR-053 model automatic viscometer supplied by Rigo Co., LTD.

(3) Melting Point (Tm(° C.)) of Copolymer by a Differential Scanning Calorimeter (DSC)

Measured with a DSC7 model differential scanning calorimeter supplied by Parkin-Elmer Inc. A sample (10 mg) was pre-melted in a nitrogen atmosphere at 230° C. for 3 minutes, and then the sample was temperature-decreased to 20° C. at a rate of 10° C./minute. The sample was maintained at this temperature for 3 minutes, and the sample was temperature-increased at a rate of 10° C./minute to obtain a melting endothermic curve, and a peak top temperature of a maximum peak of the melting endothermic curve was used as a melting point.

(4) Extraction Amount of Copolymer in Boiling Diethyl Ether (ES (wt %))

3 Grams of pellets pulverized so as to have a size of 1 mmφ mesh pass were placed in a cylinder filter, 160 ml of diethyl ether as an extraction solvent was placed in a flat-bottom flask, and Soxhlet extraction was carried out for 10 hours at a reflux frequency of approximately once/5 minutes. After completion of the extraction, diethyl ether was recovered with a rotary evaporator, and, further, the residue was dried with a vacuum dryer until a constant amount was attained, which was used as a boiling diethyl ether extraction amount.

(5) Melt Flow Rate (MFR (g/10 minutes))

Measured at a temperature of 230° C. under a load of 2,160 g according to JIS K7210.

In Examples and Comparative Examples, films were evaluated for properties according to the following methods.

All of formed films (thickness: 30 μm) were annealed at a temperature of 40° C. for 24 hours and, further, conditioned at a temperature of 23±2° C. at a humidity of 50±10% for at least 16 hours, and then the films were measured at the same temperature under the same humidity conditions.

(1) Heat Sealing Temperature

Films were measured in conformity to JIS Z-1707. Specifically, a film was sealed with a heat seal bar calibrated with a surface thermometer, left at room temperature for one day and one night and then measured for a peel strength at a peel rate of 200 mm/minute at a room temperature by a T-type peeling method. The heat sealing temperature was defined to be a temperature at which the peel strength came to be 300 g/15 mm, and it was determined from a sealing temperature-peel strength curve by calculation.

<Sealing Conditions>

Seal surface: metal roll surface/metal roll surface, sealing area: 15×10 mm, sealing pressure: 2.0 kg/cm², sealing time period: 1 second, sealing temperature: several points of temperature were used to obtain heat sealing temperature by interpolation.

Figure 5:
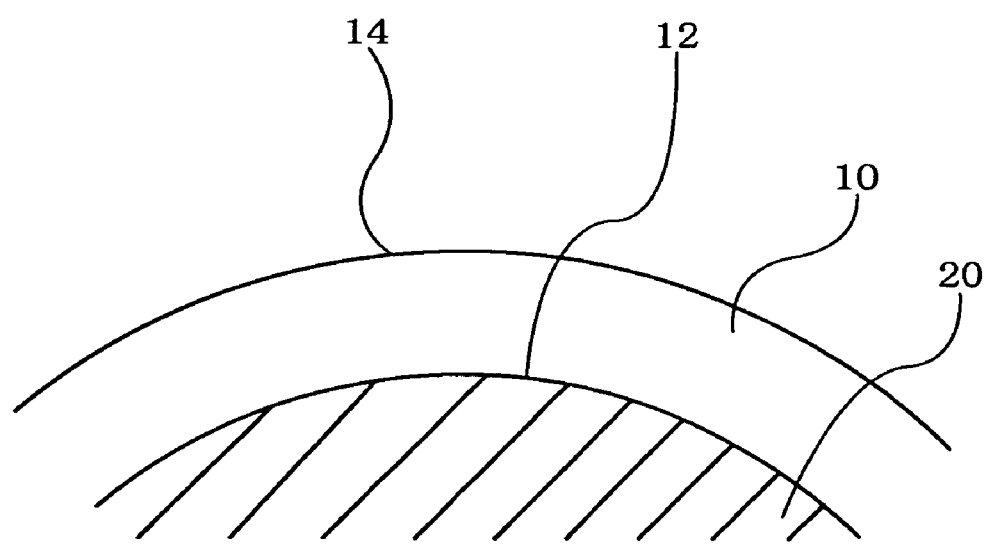
FIG. 5 is a drawing for explaining the methods of measuring the heat sealing temperature and anti-blocking property of films prepared in Examples.

FIG. 5 shows a film-preparing step. A film 10 contacts a metal roll 20. Apparently from FIG. 5, the film 10 has the surface 12 that contacted the metal roll 20 and the surface 14 that did not contact the roll 20. The surface 12 is smoother. The above "metal roll surface/metal roll surface" means that the surface that contacted the metal roll of a film was sealed to the surface that contacted the metal roll of the other film.

(2) Anti-Blocking Property

Two films were hermetically contacted to each other such that the metal roll surface (surface that contacted a metal roll) of a film contacted the anti-metal roll surface (surface that did not contact a metal roll) of the other film under the following conditions. The films contacted were fixed to 10×10 cm tools, and measured for a hermetically bonding strength of a 10×10 cm area by a peel test under the following conditions.

Hermetically contacting condition 1:

Temperature: 60° C., 3 hours, a load of 36 g/cm², an area of 10×10 cm

Hermetically contacting condition 2:

Temperature: 50° C., 7 days, a load of 15 g/cm², an area of 10×10 cm

Peel test conditions

Test speed: 20 mm/minute load cell: 2 kg (3) Impact Resistance

Evaluated on the basis of the impact fracture strength using a ½ inch impacter in a film impact tester of Toyo Seiki Seisaku-sho, Ltd.

(4) Tensile Modulus

Measured by a tensile test in conformity to JIS K7127 under the following conditions.

Crosshead speed: 500 mm/minute

Load cell: 10 kg

Measurement direction: in machine direction (MD)

Example 13

(1) Preparation of Magnesium Compound

A reactor made of glass having an internal volume of 5 liters and having a stirrer was flushed with nitrogen, and 2,250 ml (38.6 mol) of dehydrated ethanol, 113 ml (1.2 mol) of n-butanol, 12 g (95 milligram atom) of iodine and 120 g (4.9 gram atom) of metal magnesium were poured into the reactor and allowed to react at a reflux temperature (79° C.) with stirring (350 rpm) until no hydrogen was generated from the system. Unreacted alcohol was removed, and a magnesium compound was obtained.

The above magnesium compound had an $Mg(OEt)_{2-n}(OR)_n$ composition of $Mg(OC_2H_5)_{1.94}(OC_4H_9)_{0.06}$.

(2) Preparation of Solid Catalyst Component

A reactor made of glass having an internal volume of 5 liters and having a stirrer was flushed with nitrogen, and 160 g of the magnesium compound obtained in the above (1) and 800 ml of dehydrated octane were placed in the reactor. The mixture was heated to 40° C., 24 ml (230 mmol) of silicon tetrachloride was added, the mixture was stirred for 20 minutes, and 34 ml (130 mmol) of di-n-butyl phthalate was added. The resultant solution was temperature-increased up to 80° C., and then 770 ml (7 mol) of titanium tetrachloride was dropwise added with a dropping funnel. The internal temperature was adjusted to 125° C., and the mixture was stirred for 1 hour, which was taken as a first supporting operation. Then, the mixture was fully washed with dehydrated octane. Further, 1,220 ml (11.1 mol) of titanium tetrachloride was added, the internal temperature was adjusted to 125° C., and the mixture was stirred for 2 hours, which was taken as a second supporting operation. Then, the mixture was fully washed with dehydrated octane at 125° C., to give a solid catalyst component.

(3) Preliminary Polymerization

A reactor made of glass having an internal volume of 5 liters and having a stirrer was flushed with nitrogen, and 120 g of the solid catalyst component was poured into the reactor. Further, 940 ml of dehydrated heptane was added, and 25 ml of triethylaluminum and 31 ml of dicyclopentyldimethoxysilane were added. The internal temperature was adjusted to 50° C., and propylene gas was circulated and reacted under atmospheric pressure for 2 hours. Then, the solid catalyst component was fully washed with dehydrated heptane to give a preliminary polymerization catalyst A.

(4) Regular Polymerization

The above preliminary polymerization catalyst component A, triethylaluminum and dicyclopentyldimethoxysilane were continuously fed to a polymerization vessel having an internal volume of 200 liters and having a stirrer, and propylene and ethylene were reacted in the co-presence of hydrogen at a polymerization temperature of 80° C. under a polymerization pressure of 2.8 MPa. The feed amount of the solid catalyst was adjusted so as to attain a polymerization rate of 30 kg/hour in the polymerization vessel, and the feed amounts of triethylaluminum and dicyclopentyldimethoxysilane were adjusted to attain 4 mmol/kg polymer and 0.4 mmol/kg polymer, respectively. The feed amounts of propylene and ethylene were adjusted such that a formed polymer had an ethylene content of 4 wt %, and the feed amount of hydrogen was adjusted so as to attain an MFR of about 7. In the polymerization vessel, ethylene had a concentration of 3.4 mol %, and hydrogen had a concentration of 6.8 mol %.

In the thus-obtained propylene random copolymer powder, the content of a crude powder having a diameter of 4 mm or more was 0.8 wt % per kg of the powder, and the powder was stably withdrawn.

The obtained propylene random copolymer powder was measured for resin properties by the foregoing methods and measured for flow properties (flowability) of particles by the following method. Table 3 shows the results.

Additives formulated as shown in the following (A) were added to the obtained propylene random copolymer powder, and the mixture was pelletized with a model 135B extruder supplied by Toshiba Machine Co., Ltd. The obtained propylene random copolymer pellets were molded into a film having a thickness of 30 μm with a 75 mmφ extruder supplied by Mitsubishi Heavy Industries, Ltd. under conditions including a resin temperature, at a T-die outlet, of 243° C., a chill roll temperature of 40° C. and a take-up rate of 125 m/minute.

The thus-obtained film was evaluated for properties. Table 3 shows the results.

<Formulated Additives (A)>

Antioxidant:
 Irganox 1010 (Ciba Specialty Chemicals): 1,000 ppm
 Irgafox 168: (Ciba Specialty Chemicals): 1,000 ppm
 Neutralizing agent:
 Calcium stearate: 1,000 ppm Anti-Blocking Agent:
 Silica-containing anti-blocking agent (Fuji Silicia): 2,300 ppm
 Slip agent:
 Erucic acid amide: 500 ppm Comparative Example 5

(1) Preparation of Magnesium Compound

Example 13(1) was repeated except that the n-butanol was replaced with 2,300 ml (39.4 mol) of ethanol.

The thus-obtained magnesium compound was analyzed in the same manner as in Example 13(1) to show that it had a composition of $Mg(OC_2H_5)_2$.

(2) Preparation of Solid Catalyst Component

Example 13(2) was repeated except that the contact reaction temperature was changed from 125° C. to 110° C. and further that the step of washing with dehydrated heptane at 125° C. was changed to the step of washing with dehydrated heptane at 80° C.

(3) Preliminary Polymerization

A preliminary polymerization catalyst component B was obtained in the same manner as in Example 13(3) except that the solid catalyst component was replaced with the solid catalyst component obtained in Comparative Example 5(2).

(4) Regular Polymerization

Examples 13(4) was repeated except that the preliminary polymerization catalyst component was replaced with the preliminary polymerization catalyst component prepared in Comparative Example 5(3), that the ethylene concentration in the polymerization vessel was changed to 3.3 mol % and that the hydrogen concentration in the polymerization vessel was changed to 6.5 mol %.

In the obtained propylene random copolymer powder, the content of a crude power having a diameter of 4 mm or greater was 2.8 wt %, and a failure in withdrawing the powder took place frequently.

A film was prepared from the obtained propylene random copolymer powder and evaluated for properties as in Example 13(4). Table 3 shows the results.

Example 14

Regular polymerization was carried out in the same manner as in Example 13(4) except that the preliminary polymerization catalyst A prepared in Example 13(3) was used, that the ethylene concentration in the polymerization vessel was changed to 4.1 mol % and that the hydrogen concentration in the polymerization vessel was changed to 8.2 mol %.

In the thus-obtained propylene random copolymer powder, the content of a crude powder having a diameter of 4 mm or greater was 1.0 wt %, and the powder was stably withdrawn.

A film was prepared from the propylene random copolymer powder and evaluated in the same manner as in Example 13(4). Table 3 shows the results.

Comparative Example 6

Comparative Example 5(4) was repeated except that the preliminary polymerization catalyst component B prepared in Comparative Example 5(3) was used and that the ethylene concentration in the polymerization vessel in the regular polymerization was changed to 4.0 mol % and the hydrogen concentration in the polymerization vessel in the regular polymerization was changed to 8.3 mol %. During the regular polymerization, the powder came to be withdrawable, and the operation was terminated.

Example 15

A powder was obtained in the same manner as in Example 13 except that the ethylene concentration in the polymerization vessel in the regular polymerization was changed to 1.6 mol % and that the hydrogen concentration in the polymerization vessel in the regular polymerization was changed to 6.3 mol %.

In the thus-obtained propylene random copolymer powder, the content of a crude powder having a diameter of 4 mm or greater was 0.5 wt %, and the powder was stably withdrawn.

Further, a film was formed in the same manner as in Example 13 except that the formulated additives were replaced with formulated additives shown in the following (B) and that a film having a thickness of 30 μm was formed with a 75 mmφ extruder supplied by Mitsubishi Heavy Industries, Ltd. under conditions of a resin temperature, at a T-die outlet, of 265° C., a chill roll temperature of 25° C. and a take-up rate of 150 m/minute.

The obtained propylene random copolymer powder and the film were evaluated in the same manner as in Example 13(4). Table 3 shows the results.

<Formulated Additives (B)>

Antioxidant:
  Irganox 1010 (Ciba Specialty Chemicals): 1,000 ppm
  Irgafox 168: (Ciba Specialty Chemicals): 1,000 ppm
Neutralizing agent:
  Calcium stearate: 1,000 ppm
Anti-blocking agent:
  Silica-containing anti-blocking agent (Fuji Silicia): 1,000 ppm
Slip agent:
  Erucic acid amide: 250 ppm (2) Measurement of [η]

Measured according to the foregoing method.

(3) Measurement for Amount of Component Soluble in Room-Temperature Xylene

Components soluble and insoluble in room-temperature (25° C.) xylene were determined as follows.

(a) A sample in an amount of 5±0.05 g was weighed and placed in a 1,000 ml eggplant type flask, 1±0.05 g of BHT (antioxidant) was added further, and a rotor and 700±10 ml of p-xylene were poured into the mixture.

(b) a condenser was attached to the eggplant type flask, and while the rotor was operated, the flask was heated in a 140±5° C. oil bath for 120±30 minutes to dissolve the sample in the p-xylene.

TABLE 3

| | | Example 13 | Example 14 | Example 15 | Com. Example 5 | Com. Example 6 |
|---|---|---|---|---|---|---|
| Support | Smoothness (Sm) | 1.12 | 1.12 | 1.12 | 1.23 | 1.23 |
| Regular polymerization conditions | Temperature (° C.) | 80 | 80 | 80 | 80 | 80 |
| | Pressure (MPa) | 2.8 | 2.8 | 2.8 | 2.8 | 2.8 |
| | Ethylene concentration (mol %) | 3.4 | 4.1 | 1.6 | 3.3 | 4.0 |
| Properties of particles | Hydrogen concentration (mol %) | 6.8 | 8.2 | 6.3 | 6.5 | 8.3 |
| Operation performance | Average particle diameter (mm) | 2.11 | 2.05 | 2.22 | 1.8 | — |
| | Particles having a diameter of 4 mm or greater (wt %) | 0.8 | 1.0 | 0.5 | 2.8 | — |
| | Clogging during withdrawal | No | No | No | Frequently | Clogged, operation stopped |
| | FA (ml/sec) | 86 | 84 | 90 | 76 | — |
| Resin Properties | Propylene content (wt %) (X) | 95.8 | 95.1 | 98.0 | 95.9 | — |
| | Ethylene content (wt %) | 4.2 | 4.9 | 2.0 | 4.1 | — |
| | [η](dl/g) | 1.6 | 1.6 | 1.7 | 1.7 | — |
| | MFR(g/10 min) | 7.2 | 7.5 | 6.7 | 6.9 | — |
| | Tm(° C.) | 137.2 | 129.6 | 146.7 | 136 | — |
| | ES(wt %) | 1.4 | 1.8 | 0.9 | 2.0 | — |
| | 0.6exp{0.25(100 − X)} | 1.7 | 2.0 | 1.0 | 1.7 | — |
| Film properties | Heat-sealing temperature (° C.) | 127 | 122 | 138 | 132 | — |
| | Anti-blocking properties(N/m²) Condition 1 | 7 | 11 | 25 | 10 | — |
| | Condition 2 | 6 | 8 | 13 | 8 | — |
| | Film impact (kJ/m) | 22 | 25 | 13 | 21 | — |
| | Tensile modulus (MPa) | 880 | 770 | 1000 | 840 | — |

[Preparation of Propylene Block Copolymer]

In Examples and Comparative Examples, supports were evaluated for properties by the following method.

(1) n of $Mg(OEt)_{2-n}(OR)_n$

Measured according to the foregoing method.

(2) Average Particle Diameter of Magnesium Compound ($D_{50}$)

Measured by the foregoing method.

(3) Smoothness (Sm) of Magnesium Compound

Measured according to the foregoing method.

In Examples and Comparative Examples, particles and resins were evaluated for properties by the following methods.

(1) Flowability

Measured according to the foregoing method.

(c) Then, the contents in the flask was poured into a 1,000 ml beaker, and then, while the solution in the beaker was stirred with a stirrer, the solution was allowed to cool (for 8 hours or longer) to room temperature (25° C.). Then, a precipitate was recovered by filtering with a wire mesh.

(d) A filtrate was further filtered with a filter paper, the resultant filtrate was poured into 2,000±100 ml of methanol placed in a 3,000 ml beaker, and while the resultant mixture was stirred with a stirrer, the mixture was left at room temperature (25° C.) for 2 hours or more.

(e) Then, a precipitate was recovered by filtering with a wire mesh, air-dried for 5 hours or more and then dried with a vacuum-dryer at 100±5° C. for 240 to 270 minutes, followed by the recovery of a component soluble in room-temperature xylene The content (A) of a component soluble in room-temperature xylene is represented by A (wt %)=100×C/W, in which W(g) is the weight of the sample and C(g) is the weight of a recovered soluble component. The content of a component insoluble in the room-temperature xylene is calculated according to the expression of (100-A) % by weight.

(4) Measured of component soluble in room-temperature xylene for ethylene content and propylene content according to $^{13}$C-NMR An ethylene unit content and a propylene unit content in a component soluble in room-temperature xylene were measured according to the foregoing method.

In Examples and Comparative Examples, pellets were evaluated for properties according to the following methods.

(1) Measurement for Impact Strength

An injection molded product having a temperature of 23° C. was measured for a notched Izod impact strength at −30° C. in conformity with JIS K7110.

(2) Measurement for Flexural Modulus

Measured for a flexural modulus in conformity with JIS K7203.

Example 16

(1) Preparation of Magnesium Compound

A three-necked flask having an internal volume of 0.5 liter and having a stirrer was flushed with nitrogen, and 225 ml (3.86 mol) of dehydrated ethanol, 11.3 ml (0.12 mol) of n-butanol, 1.20 g (9.5 milligram atom) of iodine and 12.0 g (0.49 milligram atom) of metal magnesium were poured into the three-necked flask, and allowed to react at a reflux temperature (79° C.) with stirring (350 rpm) until no hydrogen was generated from the system. Unreacted alcohol was removed, to give a magnesium compound.

The above magnesium compound had a composition of $Mg(OC_2H_5)_{1.94}(OC_4H_9)_{0.06}$.

(2) Preparation of Solid Catalyst Component

A three-necked flask having an internal volume of 0.5 liter and having a stirrer was flushed with nitrogen, and 16 g of the magnesium compound obtained in the above (1) and 80 ml of dehydrated octane were placed in the three-necked flask. The mixture was heated up to 40° C., 2.4 ml (23 mmol) of silicon tetrachloride was added, the mixture was stirred for 20 minutes, and 3.4 ml (13 mmol) of di-n-butyl phthalate was added. The resultant solution was temperature-increased up to 80° C., and then 77 ml (0.70 mol) of titanium tetrachloride was dropwise added with a dropping funnel. The internal temperature was adjusted to 125° C., and the mixture was stirred for 1 hour, which was taken as a supporting operation. Then, the reaction product was fully washed with dehydrated octane. Further, 122 ml (1.11 mol) of titanium tetrachloride was added, the internal temperature was adjusted to 125° C., and the mixture was stirred for 2 hours, which was taken as a second supporting operation. Then, the reaction product was fully washed with dehydrated octane, to give a solid catalyst component.

(3) Preliminary Polymerization

A three-necked flask having an internal volume of 0.5 liter and having a stirrer was flushed with nitrogen, and 6.0 g of the solid catalyst component was placed in the three-necked flask. Further, 49 ml of dehydrated heptane was added, and 1.2 ml of triethylaluminum and 0.5 ml of dicyclopentyldimethoxysilane were added. The internal temperature was adjusted to 50° C., and propylene gas was circulated under atmospheric pressure to allow it to react for 2 hours. Then, the reaction product was fully washed with dehydrated heptane to give a preliminary polymerization catalyst A.

(4) Regular Polymerization

An autoclave made of stainless steel having an internal volume of 5 liters and having a stirrer was fully dried, and 30 g of a polypropylene powder was placed in the autoclave, the autoclave was internally vacuumed, then, a propylene gas was substituted up to an ambient pressure, and the internal temperature was increased up to 70° C. The internal pressure was adjusted to 0.05 MPa (gauge), then, hydrogen gas was charged up to 0.55 MPa (gauge), and further, the pressure was gradually increased up to 2.8 MPa (gauge) with a propylene gas. Then, 10 ml of heptane, 4.0 mmol of triethylaluminum, 0.5 mmol of dicyclopentyldimethoxysilane, and 0.01 mmol, as a Ti atom, of the preliminary polymerization catalyst A were sampled into 60 ml of a catalyst-chargeable tube that had been flushed with nitrogen gas, and then poured into the autoclave to carry out polymerization for 30 minutes. Then, the pressure in the autoclave was decreased to ambient pressure, a nitrogen atmosphere was substituted, followed by vacuuming and deaeration, and then a hydrogen gas was introduced up to ambient pressure. Further, ethylene gas/propylene gas were charged at a molar ratio of 4.5:5.5 up to 1 MPa, and while the atmosphere in the autoclave was maintained at 70° C. and 1 MPa, propylene/ethylene copolymerization was carried out for 100 minutes, followed by deaeration to ambient atmosphere and the decreasing of the temperature to room temperature, and then, the autoclave was opened, to recover formed polymer particles.

The thus-obtained propylene-ethylene block copolymer particles were analyzed as described above. Then, 1,000 ppm of calcium stearate (NOF Corporation) as a neutralizing agent, 1,500 ppm of DHT-4A (supplied by Kyowa Chemical Industry Co., Ltd.) as a neutralizing agent, 750 ppm of P-EPQ (supplied by Clariant Corporation) as an antioxidant, 1,500 ppm of Irganox 1010 (supplied by Ciba Specialty Chemicals) as an antioxidant and 2,000 ppm of PTBBA-A1 (supplied by Dainippon Ink And Chemicals, Inc.) as a crystal nucleation agent were added to the propylene-ethylene block copolymer particles, and these were fully mixed. The mixture was melted, kneaded and granulated with a 20 mm single-screw kneading extruder, to prepare pellets. The pellets were injection-molded to prepare test pieces, and the test pieces were measured for properties.

Example 17

Example 16(4) was repeated except that the preliminary polymerization catalyst A prepared in Example 16 was used, that the amount of triethylaluminum was changed to 2.0 mmol and that the propylene/ethylene copolymerization time period was changed to 60 minutes.

Comparative Example 7

(1) Preparation of Magnesium Compound

Example 16(1) was repeated except that no n-butanol was used and that 230 ml (3.94 mol) of ethanol was used.

The thus-obtained magnesium compound had a composition of $Mg(OC_2H_5)_2$.

(2) Preparation of Solid Catalyst Component

Example 16(2) was repeated except that the above magnesium compound was used.

(3) Preliminary Polymerization

A preliminary polymerization catalyst was obtained in the same manner as in Example 16(3) except that the above solid catalyst component was used.

(4) Polymerization

Example 16(4) was repeated except that the above preliminary polymerization catalyst B was used.

Comparative Example 8

Example 17(4) was repeated except that the preliminary polymerization catalyst B prepared in Comparative Example 7 was used.

Table 4 shows the evaluation results of the above examples and comparative examples.

TABLE 4

|  |  |  | Example 16 | Com. Example 7 | Example 17 | Com. Example 8 |
|---|---|---|---|---|---|---|
| Conditions for preparation of support | EtOH/Mg | (molar ratio) | 7.75 | 8.00 | 7.75 | 8.00 |
|  | BuOH/Mg | (molar ratio) | 0.25 | 0.00 | 0.25 | 0.00 |
|  | BuOH/EtOH | (molar ratio) | 0.032 | 0.000 | 0.032 | 0.000 |
|  | n: $Mg(OEt)_{2-n}(OBu)_n$ |  | 0.06 | 0.00 | 0.06 | 0.00 |
|  | Halogen species |  | $I_2$ | $I_2$ | $I_2$ | $I_2$ |
|  | $I_2$/Mg | (gram atom ratio) | 0.019 | 0.019 | 0.019 | 0.019 |
|  | Reaction temperature | (° C.) | 79 | 78 | 79 | 78 |
|  | Number of rotation | (rpm) | 350 | 350 | 350 | 350 |
|  | $D_{50}$ | (μm) | 61 | 63 | 61 | 63 |
|  | Smoothness | (Sm) | 1.12 | 1.23 | 1.12 | 1.23 |
| Properties of resin and particles | Portion insoluble in room-temperature xylene | Ratio wt % | 60 | 62 | 79 | 81 |
|  |  | [η] dl/g | 1.15 | 1.16 | 1.12 | 1.10 |
|  |  | mmmm mol % | 98.1 | 97.9 | 98.0 | 98.1 |
|  | Portion soluble in room-temperature xylene | (A)Ratio wt % | 40 | 38 | 21 | 19 |
|  |  | (B)[η] dl/g | 2.6 | 2.7 | 2.8 | 2.8 |
|  | Propylene content | wt % | 66 | 65 | 63 | 62 |
|  | Flowability (FA) | ml/second | 76 | 66 | 89 | 79 |
|  | 100 − 1.8 × A/B |  | 72 | 75 | 86 | 88 |
| Properties | Flexural modulus | Mpa | 550 | 620 | 1350 | 1410 |
|  | Izod | (23° C.) kJ/m² | 71 | 68 | 16 | 14 |
|  |  | (−30° C.) kJ/m² | 8 | 8 | 5 | 4 |

INDUSTRIAL UTILITY

The magnesium compound of the present invention is suitable as a support for a solid catalyst component for olefin polymerization.

The propylene random copolymer obtained according to the present invention can give a film and a sheet of which sticking components are small in content and which are excellent in low-temperature heat-sealability and impact resistance.

The propylene block copolymer of the present invention is excellent in rigidity (toughness) and impact resistance and is useful in the fields of automobile parts, consumer electric and electronic parts and articles of food.

This application claims convention priorities from Japanese Patent Applications Nos. 2004-128153, 2004-243595, 2004-252958 and 2004-266256, and the contents of these applications are incorporated herein by reference.

The invention claimed is:

1. A method of producing a magnesium compound represented by formula (I), $$Mg(OC_2H_5)_{2-n}(OR^1)_n \qquad (I)$$

where
$R^1$ is $C_mH_{2m+1}$, where m is an integer of from 3 to 10, and n is a numerical value satisfying 0<n<0.35, which method comprises charging and reacting:
i) metal magnesium,
ii) ethanol,
iii) an alcohol having from 3 to 10 carbon atoms, and
iv) at least one of a halogen and a halogen-containing compound containing at least 0.0001 gram atom of a halogen atom relative to one gram of the metal magnesium, wherein
the molar ratio of component iii)/component ii) is from 0.001 to 0.3 based on the total amount of the components ii) and iii).

2. The method according to claim 1, wherein n is a numerical value of from 0.005 to 0.3.

3. The method according to claim 1, wherein a smoothness, Sm, represented by expression (1) of said magnesium compound is less than 1.20:

$$Sm=(L^1/L^2)^3 \qquad (1)$$

where
$L^1$ is a circumferential length of a projection view of a magnesium compound particle determined by photographing with a scanning electron microscope and thereafter an image-processing, and
$L^2$ is a circumferential length of an ellipse which has an area equal to the projection area of the magnesium compound particle and which is approximated to the outline of the magnesium compound particle such that when the magnesium compound particle is wrapped over the ellipse, the sum of the areas inside and outside the outline of the ellipse among the sections surrounded by the outline of the magnesium compound particle and the outline of the ellipse becomes minimum.

4. The method according to claim 1, wherein the alcohol is n-butanol.

5. The method according to claim 1, wherein the halogen is iodine, and the halogen-containing compound is magnesium chloride.

* * * * *